(12) United States Patent
Lim et al.

(10) Patent No.: US 6,461,391 B1
(45) Date of Patent: Oct. 8, 2002

(54) PRIMARY INTERMEDIATES FOR OXIDATIVE COLORATION OF HAIR

(75) Inventors: Mu-III Lim, Trumbull; Yuh-Guo Pan, Stamford, both of CT (US)

(73) Assignee: Clairol Incorporated, Stamford, CT (US)

( * ) Notice: Subject to any disclaimer, the term of this patent is extended or adjusted under 35 U.S.C. 154(b) by 0 days.

(21) Appl. No.: 10/011,804

(22) Filed: Dec. 5, 2001

Related U.S. Application Data

(63) Continuation-in-part of application No. 09/874,080, filed on Jun. 6, 2001, now abandoned, which is a continuation-in-part of application No. 09/730,707, filed on Dec. 6, 2000.

(51) Int. Cl.[7] .................................................. A61K 7/13
(52) U.S. Cl. ........................ 8/405; 8/405; 8/406; 8/409; 8/410; 548/557
(58) Field of Search ............................ 8/405, 406, 409, 8/410; 548/557

(56) References Cited

U.S. PATENT DOCUMENTS 6,042,620 A   3/2000   Braun and Chassot ........ 8/410

*Primary Examiner*—Gregory Delcotto
*Assistant Examiner*—Eisa Elhilo
(74) *Attorney, Agent, or Firm*—Charles J. Zeller

(57) ABSTRACT

Primary intermediates useful hair coloring systems comprise quaternized pyrrolidine compounds. The invention provides new quaternized pyrrolidine of Formula (1):

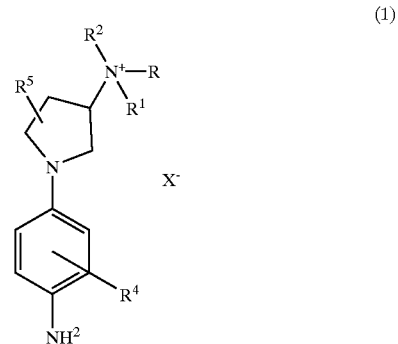

wherein X is Cl, Br, I, or $R^3SO_4$; R is a $C_1$ to $C_{22}$ alkyl group or a $C_1$ to $C_{22}$ mono or dihydroxyalkyl group; $R^1$ and $R^2$ are each independently a $C_1$ to $C_4$ alkyl group; $R^3$ is a $C_1$ to $C_{22}$ alkyl group or a $C_1$ to $C_{22}$ mono or dihydroxyalkyl group; $R^4$ is a hydrogen atom, a $C_1$ to $C_5$ alkyl group or such an alkyl group substituted with one or more hydroxy or amino moieties; and $R^5$ is a hydrogen atom or a hydroxy group.

20 Claims, No Drawings

PRIMARY INTERMEDIATES FOR OXIDATIVE COLORATION OF HAIR

CROSS-REFERENCE TO RELATED APPLICATIONS

This is a continuation-in-part of U.S. patent application Ser. No. 09/874,080 filed Jun. 6, 2001, now abandoned which is a continuation in part of U.S. patent application Ser. No. 09/730,707 filed Dec. 6, 2000.

FIELD OF THE INVENTION

This invention relates to new quaternized pyrrolidine compounds and compositions containing these compounds as primary intermediates for oxidative coloring of hair fibers.

BACKGROUND TO THE INVENTION

Coloration of hair is a procedure practiced from antiquity employing a variety of means. In modern times, the method most extensively to color hair is an oxidative dyeing process utilizing one or more oxidative hair coloring agents in combination with one or more oxidizing agents.

Most commonly a peroxy oxidizing agent is used in combination with one or more oxidative hair coloring agents, generally small molecules capable of diffusing into hair and comprising one or more primary intermediates and one or more couplers. In this procedure, a peroxide material, such as hydrogen peroxide, is employed to activate the small molecules of primary intermediates so that they react with couplers to form larger sized compounds in the hair shaft to color the hair in a variety of shades and colors.

A wide variety of primary intermediates and couplers have been employed in such oxidative hair coloring systems and compositions. Among the primary intermediates employed there may be mentioned p-phenylenediamine, p-toluenediamine, p-aminophenol, 4-amino-3-methylphenol, N,N-bis(2-hydroxyethyl)-p-phenylene diamine, 1-(2-hydroxyethyl)4,5-diaminopyrazole and as couplers there may be mentioned resorcinol, 2-methylresorcinol, 3-aminophenol, 2,4-diaminophenoxyethanol, and 5-amino-2-methylphenol.

There are numerous additional requirements for oxidation dye compounds that are used to dye human hair besides the color or the desired intensity. Thus, the dye compounds must be unobjectionable in regard to toxicological and dermatological properties and must provide the desired hair color with a good light fastness, fastness to a permanent wave treatment, acid fastness and fastness to rubbing. The color of the hair dyed with the dye compounds in each case must be stable for at least 4 to 6 weeks to light, rubbing and chemical agents. Furthermore, an additional requirement is the production of a broad palette of different color shades using different developer and coupler substances. A majority of the desired shades have been produced with dyes based on p-phenylenediamine. However, use of p-phenylenediamine is being questioned, mainly due to a sensitization potential. GB 2,239,265A describes that some individuals are becoming sensitized to p-phenylenediamine and its derivatives. The proposed replacements for p-phenylenediamine have not proved entirely satisfactory. There is therefore a need for new primary intermediate compounds to meet one or more of the desired properties but not possessing the sensitization potential possessed by p-phenylenediamine, that is, which has a significantly weaker sensitization potential than p-phenylenediamine.

SUMMARY OF THE INVENTION

It is therefore an object of this invention to provide new primary intermediate compounds useful in place of p-phenylenediamine to provide a wide range of different color shades with various combinations of primary intermediates and couplers, but which has a weaker sensitization potential than p-phenylenediamine.

It has been discovered that new quaternized pyrrolidine compounds are suitable primary intermediates for hair coloring compositions and systems for providing good oxidative coloration of hair and for providing acceptable light fastness, fastness to shampooing, fastness to permanent wave treatment, and suitable for providing a wide variety of different color shades with various primary intermediate and coupler compounds, but which presents a significantly weaker sensitization potential than p-phenylenediamine.

The invention provides new quaternized pyrrolidine compounds of Formula (1):

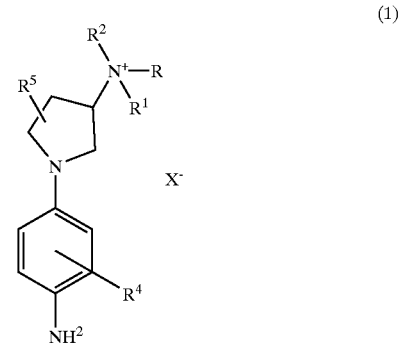

wherein X is Cl, Br, I, or $R^3SO_4$; R is a $C_1$ to $C_{22}$ alkyl group or a $C_1$ to $C_{22}$ mono or dihydroxyalkyl group; $R^1$ and $R^2$ are each independently a $C_1$ to $C_4$ alkyl group; $R^3$ is a a $C_1$ to $C_{22}$ alkyl group or a $C_1$ to $C_{22}$ mono or dihydroxyalkyl group; $R^4$ is a hydrogen atom, a $C_1$ to $C_5$ alkyl group or such an alkyl group substituted with one or more hydroxy or amino moieties; and $R^5$ is a hydrogen atom or a hydroxy group.

DETAILED DESCRIPTION OF THE INVENTION

The new quaternized pyrrolidine compounds of this invention can be prepared by the reaction of a suitable N-(4-nitrophenyl)-3-amino pyrrolidine with a quaternization reagent (R-X) in a suitable solvent such as dimethylformamide (DMF) to produce a quaternized salt which can be precipitated out with diethyl ether, followed by hydrogenation of the salt with hydrogen in anhydrous methanol and a suitable hydrogenation catalyst according to the following reaction sequence where R, $R^1$, $R^2$, $R^3$, $R^4$, $R^5$ and X are as defined hereinbefore.

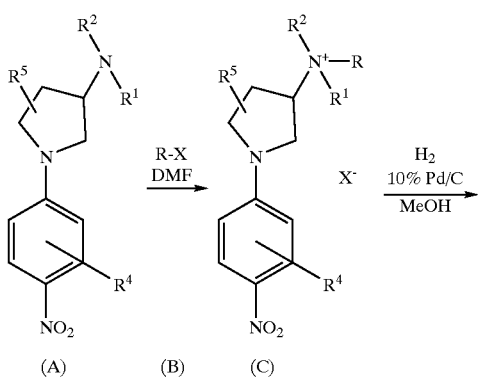

(A)    (B)    (C)

(1)

A sample synthesis procedure is as follows. Compound A (0.47 g, 2.0 mmol) is dissolved in anhydrous DMF (2.0 mL). To this is added the desired quaternization reagent B of the formula R-X. The reaction mixture is stirred at 60° C. for about 18 hrs. and cooled to room temperature. Diethyl ether (25 mL) is added to precipitate out the salt C. Salt C is hydrogenated at 60 psi in anhydrous methanol in the presence of 10% Pd/C catalyst at room temperature for 18 hrs. The reaction is then filtered through a pad of Celite and evaporated in vacuo to provide the compounds of Formula (1) of this invention.

The quaternized pyrrolidine compounds of this invention can be employed in dye compositions and systems of this invention in an amount of from about 0.005 to about 20, preferably from about 0.01 to about 5.0, and most preferably from about 0.1 to about 2.5 weight percent based on the weight of the hair coloring composition.

Although advantageous properties of the above-described quaternized pyrrolidine compounds of this invention can be obtained when they are employed as the sole primary intermediate in hair coloring compositions or systems of this invention, it is to be recognized that these quaternized pyrrolidine compounds may be employed together with one or more other suitable primary intermediates.

Examples of such other suitable primary intermediates include: p-phenylenediamine derivatives such as: benzene-1,4-diamine, 2-methyl-benzene-1,4-diamine, 2-chloro-benzene-1,4-diamine, N-phenyl-benzene-1,4-diamine, N-(2-ethoxyethyl)benzene-1,4-diamine, 2-[(4-amino-phenyl)-(2-hydroxy-ethyl)-amino]-ethanol, (2,5-diamino-phenyl)-methanol, 1-(2,5-diamino-phenyl)-ethanol, 2-(2,5-diamino-phenyl)-ethanol, N-(4-aminophenyl)benzene-1,4-diamine, 2,6-dimethyl-benzene-1,4-diamine, 2-isopropyl-benzene-1,4-diamine, 1-[(4-aminophenyl)amino]-propan-2-ol, 2-propyl-benzene-1,4-diamine, 1,3-bis[(4-aminophenyl)(2-hydroxyethyl)amino]propan-2-ol, $N^4,N^4,2$-trimethylbenzene-1,4-diamine, 2-methoxy-benzene-1,4-diamine, 1-(2,5-diaminophenyl)ethane-1,2-diol, 2,3-dimethyl-benzene-1,4-diamine, N-(4-amino-3-hydroxy-phenyl)-acetamide, 2,6-diethylbenzene-1,4-diamine, 2,5-dimethylbenzene-1,4-diamine, 2-thien-2-ylbenzene-1,4-diamine, 2-thien-3-ylbenzene-1,4-diamine, 2-pyridin-3-ylbenzene-1,4-diamine, 1,1'-biphenyl-2,5-diamine, 2-(methoxymethyl)benzene-1,4-diamine, 2-(aminomethyl)benzene-1,4-diamine, 2-(2,5-diaminophenoxy)ethanol, N-[2-(2,5-diaminophenoxy)ethyl]-acetamide, N,N-dimethylbenzene-1,4-diamine, N, N-diethylbenzene-1,4-diamine, N,N-dipropylbenzene-1,4-diamine, 2-[(4-aminophenyl)(ethyl)amino]ethanol, 2-[(4-amino-3-methyl-phenyl)-(2-hydroxy-ethyl)-amino]-ethanol, N-(2-methoxyethyl)-benzene-1,4-diamine, 3-[(4-aminophenyl)amino]propan-1-ol, 3-[(4-aminophenyl)-amino]propane-1,2-diol, N-{4-[(4-aminophenyl)amino]butyl}benzene-1,4-diamine, and 2-[2-(2-{2-[(2, 5-diaminophenyl)oxy]ethoxy}ethoxy)ethoxy]benzene-1,4-diamine;

p-aminophenol derivatives such as: 4-amino-phenol, 4-methylamino-phenol, 4-amino-3-methyl-phenol, 4-amino-2-hydroxymethyl-phenol, 4-amino-2-methyl-phenol, 4-amino-2-[(2-hydroxy-ethylamino)-methyl]-phenol, 4-amino-2-methoxymethyl-phenol, 5-amino-2-hydroxy-benzoic acid, 1-(5-amino-2-hydroxy-phenyl)-ethane-1,2-diol, 4-amino-2-(2-hydroxy-ethyl)-phenol, 4-amino-3-(hydroxymethyl)phenol, 4-amino-3-fluoro-phenol, 4-amino-2-(aminomethyl)phenol, and 4-amino-2-fluoro-phenol;

o-aminophenol derivatives such as: 2-amino-phenol, 2,4-diaminophenol, 2-amino-5-methyl-phenol, 2-amino-6-methyl-phenol, N-(4-amino-3-hydroxy-phenyl)-acetamide, and 2-amino-4-methyl-phenol; and heterocyclic derivatives such as: pyrimidine-2,4,5,6-tetramine, 1-methyl-1H-pyrazole-4,5-diamine, 2-(4,5-diamino-1H-pyrazol-1-yl)ethanol, $N^2,N^2$-dimethyl-pyridine-2,5-diamine, 2-[(3-amino-6-methoxypyridin-2-yl)amino]ethanol, 6-methoxy-N2-methyl-pyridine-2,3-diamine, 2,5,6-triaminopyrimidin-4(1H)-one, pyridine-2,5-diamine, 1-isopropyl-1H-pyrazole-4,5-diamine, 1-(4-methylbenzyl)-1H-pyrazole4,5-diamine, and 1-(4-chlorobenzyl)-1H-pyrazole-4,5-diamine.

The primary intermediates can be employed in the form of a free base or in the form of an acid additive salt thereof, such as, for example, as a hydrochloride, a hydrobromide, a sulfate or the like.

The quaternized pyrrolidine compounds of this invention alone or in combination with such other suitable primary intermediates may be employed in hair coloring compositions or systems of this invention with any suitable coupler. The coupler compounds can be employed in the hair coloring compositions or systems of this invention in an amount of from about 0.005 to about 20, preferably from about 0.01 to about 5.0, and most preferably from about 0.1 to about 2.5 weight percent based on the total weight of the hair coloring composition.

Suitable couplers include, for example, phenols, resorcinol and naphthol derivatives such as: naphthalene-1,7-diol, benzene-1,3-diol, 4-chlorobenzene-1,3-diol, naphthalene-1-ol, 2-methyl-naphthalene-1-ol, naphthalene-1,5-diol, naphthalene-2,7-diol, benzene-1,4-diol, 2-methyl-benzene-1,3-diol, 7-amino-4-hydroxy-naphthalene-2-sulfonic acid, 2-isopropyl-5-methylphenol, 1,2,3,4-tetrahydronaphthalene-1,5-diol, 2-chloro-benzene-1,3-diol, 4-hydroxy-naphthalene-1-sulfonic acid, benzene-1,2,3-triol, naphthalene-2,3-diol, 5-dichloro-2-methylbenzene-1,3-diol, 4,6-dichlorobenzene-1,3-diol, and 2,3-dihydroxy-[1,4] naphthoquinone;

m-phenylenediamines such as: 2,4-diaminophenol, benzene-1,3-diamine, 2-(2,4-diamino-phenoxy)-ethanol, 2-[(3-amino-phenyl)-(2-hydroxy-ethyl)-amino]-ethanol, 2-mehyl-benzene-1,3-diamine, 2-[[2-(2,4-diamino-phenoxy)-ethyl]-(2-hydroxy-ethyl)-amino]-ethanol, 4-{3-[(2,4-diaminophenyl)oxy] propoxy}benzene-1,3-diamine, 2-(2,4-diamino-phenyl)-ethanol, 2-(3-amino-4-methoxy-phenylamino)-ethanol, 4-(2-amino-ethoxy)-benzene-1,3-diamine, (2,4-diamino-phenoxy)-acetic acid, 2-[2,4-diamino-5-(2-hydroxy-ethoxy)-phenoxy]-ethanol, 4-ethoxy-6-methyl-benzene-1,3-diamine, 2-(2,4-diamino-5-methyl-phenoxy)-ethanol, 4,6-dimethoxy-benzene-1,3-diamine, 2-[3-(2-hydroxy-ethylamino)-2-methyl-phenylamino]-ethanol, 3-(2,4-diamino-phenoxy)-propan-1-ol, N-[3-(dimethylamino)phenyl] urea, 4-methoxy-6-methylbenzene-1,3-diamine, 4-fluoro-6-methylbenzene-1,3-diamine, 2-({3-[(2-hydroxyethyl)amino]-4,6-dimethoxyphenyl}amino) ethanol, 3-(2,4-diaminophenoxy)-propane-1,2-diol, 2-[2-amino-4-(methylamino)phenoxy]ethanol, 2-[(5-amino-2-ethoxy-phenyl)-(2-hydroxy-ethyl)-amino]-ethanol, 2-[(3-aminophenyl)amino]ethanol N-(2-aminoethyl)benzene-1,3-diamine, 4-{[(2,4-diaminophenyl)oxy]methoxy}-benzene-1,3-diamine, and 2,4-dimethoxybenzene-1,3-diamine;

m-aminophenols such as: 3-amino-phenol, 2-(3-hydroxy-4-methyl-phenylamino)-acetamide, 2-(3-hydroxy-phenylamino)-acetamide, 5-amino-2-methyl-phenol, 5-(2-hydroxy-ethylamino)-2-methyl-phenol, 5-amino-2,4-dichloro-phenol, 3-amino-2-methyl-phenol, 3-amino-2-chloro-6-methyl-phenol, 5-amino-2-(2-hydroxy-ethoxy)-phenol, 2-chloro-5-(2,2,2-trifluoro-ethylamino)-phenol, 5-amino-4-chloro-2-methyl-phenol, 3-cyclopentylamino-phenol, 5-[(2-hydroxyethyl)amino]4-methoxy-2-methylphenol, 5-amino-4-methoxy-2-methylphenol, 3-(dimethylamino)phenol, 3-(diethylamino)phenol, 5-amino-4-fluoro-2-methylphenol, 5-amino-4-ethoxy-2-methylphenol, 3-amino-2,4-dichloro-phenol, 3-[(2-methoxyethyl)amino]phenol, 3-[(2-hydroxyethyl) amino]phenol, 5-amino-2-ethyl-phenol, 5-amino-2-methoxyphenol, 5-[(3-hydroxypropyl)amino]-2-methylphenol, 3-[(3-hydroxy-2-methylphenyl)-amino] propane-1,2-diol, and 3-[(2-hydroxyethyl)amino]-2-methylphenol; and heterocyclic derivatives such as: 3,4-dihydro-2H-1,4-benzoxazin-6-ol, 4-methyl-2-phenyl-2,4-dihydro-3H-pyrazol-3-one, 6-methoxyquinolin-8-amine, 4-methylpyridine-2,6-diol, 2,3-dihydro-1,4-benzodioxin-5-ol, 1,3-benzodioxol-5-ol, 2-(1,3-benzodioxol-5-ylamino)ethanol, 3,4-dimethylpyridine-2,6-diol, 5-chloropyridine-2,3-diol, 2,6-dimethoxypyridine-3,5-diamine, 1,3-benzodioxol-5-amine, 2,6-bis(2-hydroxyethoxy)-3,5-diaminopyridine, 1H-indol4-ol, 5-amino-2,6-dimethoxypyridine-3-ol, 1H-indole-5,6-diol, 1H-indol-7-ol, 1H-indol-5-ol, 1H-indol-6-ol, 6-bromo-1,3-benzodioxol-5-ol, 2-aminopyridin-3-ol, pyridine-2,6-diamine, 3-[(3,5-diaminopyridin-2-yl)oxy]propane-1,2-diol, 5-[(3,5-diaminopyridin-2-yl)oxy]pentane-1,3-diol, 1H-indole-2,3-dione, indoline-5,6-diol, 3,5-dimethoxypyridine-2,6-diamine, 6-methoxypyridine-2,3-diamine, and 3,4-dihydro-2H-1,4-benzoxazin-6-amine.

Preferred Primary Intermediates Include:

p-phenylenediamine derivatives such as: 2-methyl-benzene-1,4-diamine, benzene-1,4-diamine, 1-(2,5-diamino-phenyl)-ethanol, 2-(2,5-diamino-phenyl)-ethanol, N-(2-methoxyethyl)benzene-1,4-diamine, 2-[(4-amino-phenyl)-(2-hydroxy-ethyl)-amino]-ethanol, and 1-(2,5-diaminophenyl)ethane-1,2-diol;

p-aminophenol derivatives such as 4-amino-phenol, 4-methylamino-phenol, 4-amino-3-methyl-phenol, 4-amino-2-methoxymethyl-phenol, and 1-(5-amino-2-hydroxy-phenyl)-ethane-1,2-diol;

o-aminophenol derivatives such as: 2-amino-phenol, 2-amino-5-methyl-phenol, 2-amino-6-methyl-phenol, N-(4-amino-3-hydroxy-phenyl)-acetamide, and 2-amino-4-methyl-phenol;

heterocyclic derivatives such as: pyrimidine-2,4,5,6-tetramine, 1-methyl-1H-pyrazole-4,5-diamine, 2-(4,5-diamino-1H-pyrazol-1-yl)ethanol, and $N^2,N^2$-dimethyl-pyridine-2,5-diamine.

Preferred Couplers Include phenols, resorcinol and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, and 2-isopropyl-5-methylphenol;

m-phenylenediamines such as: benzene-1,3-diamine, 2-(2,4-diamino-phenoxy)-ethanol, 4-{3-[(2,4-diaminophenyl)oxy]propoxy}benzene-1,3-diamine, 2-(3-amino-4-methoxy-phenylamino)-ethanol, 2-[2,4-diamino-5-(2-hydroxy-ethoxy)-phenoxy]-ethanol, and 3-(2,4-diamino-phenoxy)-propan-1-ol;

m-aminophenols such as: 3-amino-phenol, 5-amino-2-methyl-phenol, 5-(2-hydroxy-ethylamino)-2-methyl-phenol, and 3-amino-2-methyl-phenol; and heterocyclic derivatives such as: 3,4-dihydro-2H-1,4-benzoxazin-6-ol, 4-methyl-2-phenyl-2,4-dihydro-3H-pyrazol-3-one, 1,3-benzodioxol-5-ol, 1,3-benzodioxol-5-amine, 1H-indol-4-ol, 1H-indole-5,6-diol, 1H-indol-7-ol, 1H-indol-5-ol, 1H-indol-6-ol, 1H-indole-2,3-dione, pyridine-2,6-diamine, and 2-aminopyridin-3-ol.

Most Preferred Primary Intermediates Include p-phenylenediamine derivatives such as: 2-methyl-benzene-1,4-diamine, benzene-1,4-diamine, 2-(2,5-diamino-phenyl)-ethanol, 1-(2,5-diamino-phenyl)-ethanol, and 2-[(4-amino-phenyl)-(2-hydroxy-ethyl)-amino]-ethanol;

p-aminophenol derivatives such as: 4-amino-phenol, 4-methylamino-phenol, 4-amino-3-methyl-phenol, and 1-(5-amino-2-hydroxy-phenyl)-ethane-1,2-diol;

o-aminophenols such as: 2-amino-phenol, 2-amino-5-methyl-phenol, 2-amino-6-methyl-phenol, and N-(4-amino-3-hydroxy-phenyl)-acetamide; and heterocyclic derivatives such as: pyrimidine-2,4,5,6-tetramine and 2-(4,5-diamino-1H-pyrazol-1-yl)ethanol.

Most Preferred Couplers Include phenols, resorcinol and naphthol derivatives such as: benzene-1,3-diol, 4-chlorobenzene-1,3-diol, naphthalen-1-ol, 2-methyl-naphthalen-1-ol, and 2-methyl-benzene-1,3-diol;

m-phenylenediamine such as: 2-(2,4-diamino-phenoxy)-ethanol, 2-(3-amino-4-methoxy-phenylamino)-ethanol, 2-[2,4-diamino-5-(2-hydroxy-ethoxy)-phenoxy]-ethanol, and 3-(2,4-diamino-phenoxy)-propan-1-ol;

m-aminophenols such as: 3-amino-phenol, 5-amino-2-methyl-phenol, 5-(2-hydroxy-ethylamino)-2-methyl-phenol, and 3-amino-2-methyl-phenol; and heterocyclic derivatives such as: 3,4-dihydro-2H-1,4-benzoxazin-6-ol, 4-methyl-2-phenyl-2,4-dihydro-3H-pyrazol-3-one, and 1H-indol-6-ol, and 2-aminopyridin-3-ol.

The total amount of the combination of primary intermediate and coupler compounds in the hair coloring compositions or systems of this invention is generally from about 0.001 to about 10, preferably from about 0.02 to about 10 and most preferably from about 0.2 to about 6.0 weight percent based on the total weight of the hair coloring composition. The primary intermediate and coupler compounds are generally used in equivalent amounts. However, it is possible to use the primary intermediate compounds in either excess or deficiency.

The hair coloring compositions according to the invention can also contain certain other dye ingredients, for example Acid Orange 3, Disperse Orange 3, Disperse Black 9, HC Orange 1, HC Orange 2, HC Orange 3, HC Yellow 2, HC Yellow 4, HC Yellow 5, HC Yellow 6, HC Yellow 7, HC Yellow 9, HC Yellow 10, HC Yellow 11, HC Yellow 12, HC Yellow 13, HC Yellow 14, HC Yellow 15, 4-nitro-o-phenylenediamine, 2-nitro-5-glyceryl methylaniline, 4-nitrophenyl aminoethylurea, hydroxyethyl-2-nitro-p-toluidine, 3-methylamino-4-nitrophenoxyethanol, 2-amino-6-chloro-4-nitrophenol, 2-chloro-6-ethylamino-4-nitrophenol, Basic Yellow 57, Solvent Orange 45, 4-nitro-m-phenylenediamine, Natural Orange 6, 2-hydroxyethylamino-5-nitroanisole, 2-amino-3-nitrophenol, 6-nitro-o-toluidine, N-ethyl-3-nitro PABA, N-hydroxyethyl-2,6-dinitro-p-anisidine, 6-nitro-2,5-pyridinediamine, 4-chloro-5-methyl-2-nitrophenol, HC Red 1, HC Red 3, HC Red 7, HC Red 10, HC Red 11, HC Red 13, HC Red 14, 2-nitro-p-henylenediamine, 3-nitro-p-hydroxyethylaminophenol, 4-hydroxypropylamino-3-nitrophenol, 4-amino-3-nitrophenol, picramic acid, N-(2-hyroxyethyl)picramic acid, Basic Red 76, Disperse Red 17, N-methyl-3-nitro-p-phenylenediamine, 2-chloro-5-nitro-N-hydroxyethyl-p-phenylenediamine, 4-amino-2-nitrodiphenylamine-2'-carboxylic acid, 4-amino-4'-dimethylamino-2-nitrodiphenylamine-2'-carboxylic acid, Disperse Violet 1, Disperse Violet 4, HC Blue 2, HC Blue 6, HC Blue 9, HC Blue 10, HC Blue 11, HC Blue 12, HC Violet 1, HC Violet 2, N,N-bis(2-hydroxyethyl)-2-nitro-p-phenylenediamine, 2-nitro-4-[bis(2-hydroxyethyl)amino]diphenylamine, Basic Violet 14, Disperse Blue 1, Disperse Blue 3, Basic Blue 7, Basic Blue 9, Basic Blue 26, Basic Blue 17, Basic Blue 99, Basic Brown 16, Basic Brown 17, and Acid Black 1.

These dye compounds can be contained in the hair coloring composition of the invention in an amount of from about 0.1 to 4.0 percent by weight.

Understandably, the coupler compounds and the primary intermediate compounds, as well as the other dye compounds, in so far as they are bases, can also be used in the form of their physiologically compatible salts with organic or inorganic acids, such as hydrochloric acid or sulfuric acid, or, in so far as they have aromatic OH groups, in the form of their salts with bases, such as alkali phenolates.

Moreover, cosmetic additive ingredients, which are commonly used in compositions for coloring hair, can be used in the hair coloring compositions according to the invention, for example antioxidants, such as ascorbic acid, thioglycolic acid or sodium sulfite, and perfume oils, complex formers, wetting agents, emulsifiers, thickeners and care materials.

The form of the hair coloring compositions according to the invention can be, for example, a solution, especially an aqueous or aqueous-alcoholic solution. However, the form that is particularly preferred is a cream, gel or an emulsion. Its composition is a mixture of the dye ingredients with the conventional cosmetic additive ingredients suitable for the particular preparation.

Conventional cosmetic additive ingredients in solutions, creams, emulsion or gels include, for example:

Solvents: In addition to water, solvents that can be used are lower alkanols (e.g.,ethanol, propanol, isopropanol); polyols (e.g., carbitols, propylene glycol, glycerin). Under suitable processing, higher alcohols, such as cetyl alcohol, are suitable organic solvents, provided they are first liquified by melting, typically at low temperature (50 to 80 deg. C.), before incorporation of other, usuually lipophilic, materials. See WO 98/27941 (section on diluents) incorporated by reference.

Anionic and Nonionic Surfactants: These materials are from the classes of anionic, cationic, amphoteric or nonionic surfactant compounds, such as fatty alcohol sulfates, ethoxylated fatty alcohol sulfates, alkylsulfonates, alkylbenzensulfonates, alkyltrimethylammonium salts, alkylbetaines, ethoxylated fatty alcohols, ethoxylated nonylphenols, fatty acid alkanol amides and ethoxylated fatty acid esters. They are included for various reasons, e.g., to assist in thickening, for forming emulsions, to help in wetting hair during application of the hair dye composition, etc. Suitable materials are alkyl sulfates, ethoxylated alkyl sulfates, alkyl glyceryl ether sulfonates, methyl acyl taurates, acyl isethionates, alkyl ethoxy carboxylates, fatty acid mono- and diethanolamides. Reference is made to WO 98/52523 published Nov. 26, 1998 and incorporated herein by reference.

Thickeners: Suitable thickeners include such as higher fatty alcohols, starches, cellulose derivatives, petrolatum, paraffin oil, fatty acids and anionic and nonionic polymeric thickeners based on polyacrylic and polyurethane polymers. Examples are hydroxyethyl cellulose, hydroxymethylcellulose and other cellulose derivatives, hydrophobically modified anionic polymers and nonionic polymers, particularly such polymers having both hydrophilic and hydrophobic moieties (i.e., amphiphilic polymers). Useful nonionic polymers include polyurethane derivatives such as PEG-15/stearyl alcohol/SDMI copolymer and PEG-150/stearyl alcohol SDMI copolymer. Other useful amphiphilic polymers are disclosed in U.S. Pat. No. 6,010,541 incorporated by reference. Examples of anionic polymers that can be used as thickeners are acrylates copolymer, acrylates/ceteth-20 methacrylates copolymer, acrylates/ceteth-20 itaconate copolymer, and acrylates/beheneth-25 acrylates copolymer. Aculyn® polymers sold by Rohm & Haas, as well as hair care materials, such as cationic resins, lanolin derivatives, cholesterol, pantothenic acids and betaine.

Alkalizing agents: Suitable materials that are used to increase pH of the semipermanent hair dye compositions include ammonia, aminomethylpropanol, methylethanolamine, triethanolamine and ethanolamine.

Conditioners: Suitable materials include silicones and silicone derivatives; hydrocarbon oils; monomeric quaternary compounds, and quaternized polymers. Monomeric quaternary compounds are typically cationic compounds, but may also include betaines and other amphoteric and zwitterionic materials. Suitable monomeric quaternary compounds include behentrialkonium chloride, behentrimonium chloride, benzalkonium bromide or chloride, benzyl triethyl ammonium chloride, bis-hydroxyethyl tallowmonium chloride, C12–18 dialkyldimonium chloride, cetalkonium chloride, ceteartrimonium bromide and chloride, cetrimonium bromide, chloride and methosulfate, cetylpyridonium chloride, cocamidoproypl ethyidimonium ethosulfate, cocamidopropyl ethosulfate, cocoethyidimonium ethosulfate, cocotrimonium chloride and ethosulfate, dibehenyl dimonium chloride, dicetyldimonium chloride, dicocodimonium chloride, dilauryl dimonium chloride, disoydimonium chloride, ditallowdimonium chloride, hydrogenated tallow trimonium chloride, hydroxyethyl cetyl dimonium chloride, myristalkonium chloride, olealkonium chloride, soyethomonium ethosulfate, soytrimonium chloride, stearalkonium chloride, and many other compounds. See WO 98/27941 incorporated by reference. Quaternized polymers are typically cationic polymers, but may also include amphoteric and zwitterionic polymers. Useful polymers are exemplified by polyquaternium-4, polyquaternium-6, polyquaternium-7, polyquaternium-8, polyquaternium-9, polyquaternium-10, polyquaternium-22, polyquaternium-32, polyquaternium-39, polyquaternium-44 and polyquaternium-47. Silicones suitable to condition hair are dimethicone, amodimethicone, dimethicone copolyol and dimethiconol. See also WO 99/34770 published Jul. 15, 1999, incorporated by reference, for suitable silicones. Suitable hydrocarbon oils would include mineral oil.

Natural ingredients: For example, protein derivatives, aloe, camomile and henna extracts.

Other adjuvants include acidulents to lower pH, buffers, cheating agents antioxidants, sequestrants, etc. These classes of materials and other species of materials in the classes referred to above but not specifically identified that are suitable are listed in the International Cosmetics Ingredient Dictionary and Handbook, (Eighth Edition) published by The Cosmetics, Toiletry, and Fragrance Association, incorporated by reference. In particular reference is made to Volume 2, Section 3 (Chemical Classes) and Section 4 (Functions) are useful in identifying a specific adjuvant/excipient to achieve a particular purpose or multipurpose.

The above-mentioned conventional cosmetic ingredients are used in amounts suitable for their purposes. For example the wetting agents and emulsifiers are used in concentrations of from about 0.5 to 30 percent by weight, the thickeners are used in an amount of from about 0.1 to 25 percent by weight and the hair care materials are used in concentrations of from about 0.1 to 5.0 percent by weight.

The hair coloring compositions according to the invention can be weakly acidic, neutral or alkaline according to their composition. The compositions typically have pH values of from 6.8 to 11.5. Their pH can be adjusted in the basic range with ammonia. Also, organic amines can be used for this purpose, including monoethanolamine and triethanolamine, or also inorganic bases, such as sodium hydroxide and potassium hydroxide. Inorganic or organic acids can be used for adjusting the pH in the acid range, for example phosphoric acid, acetic acid, citric acid or tartaric acid.

In order to use the oxidation hair coloring composition for dyeing hair one mixes the above-described hair coloring compositions according to the invention with an oxidizing agent immediately prior to use and applies a sufficient amount of the mixture to the hair, according to the hair abundance, generally from about 60 to 200 grams.

Typically hydrogen peroxide, or its addition compounds with urea, melamine, sodium borate or sodium carbonate, can be used in the form of a 3 to 12 percent, preferably 6 percent, aqueous solution as the oxidizing agent for developing the hair dye. Oxygen can also be used as the oxidizing agent. If a 6 percent hydrogen peroxide solution is used as oxidizing agent, the weight ratio of hair coloring composition and oxidizing agent is 5:1 to 1:2, but preferably 1:1. The mixture of the oxidizing agent and the dye composition of the invention is allowed to act on the hair for about 10 to about 45 minutes, preferably about 30 minutes, at about 15 to 50 degrees Celsius, the hair is rinsed with water and dried. If necessary, it is washed with a shampoo and eventually after-rinsed with a weak organic acid, such as citric acid or tartaric acid. Subsequently the hair is dried.

The hair coloring composition according to the invention with a content of quaternized pyrrolidine compounds of Formula (1) as primary intermediate substances permits hair dyeing with outstanding color fastness, especially light fastness, fastness to washing and fastness to rubbing. The hair coloring composition according to the invention provides a broad palette of different color shades, which extend from, purple, violet to greenish yellow shades, according to the type and composition of the dye compounds in it, as shown in Table 3 hereinafter. Particularly the color shades produced have outstanding color intensity. The very good dyeing properties of the compositions according to the invention include the production of good color coverage and dyeing of virgin gray hair.

SYNTHESIS EXAMPLES 1 to 15

Synthesis of Quaternized Pyrrolidine Compounds of Formula (1)

Example 1

Preparation of 1-(4-Aminophenyl)-N,N,N-trimethylpyrrolidin-3-aminium Iodide

To a solution of [1-(4-nitrophenyl)-pyrrolidin-3-yl] dimethylamine (470 mg, 2.0 mmole) in dimethylformamide (2 mL) was added methyl iodide (567 mg., 4.0 mmole). The reaction mixture was stirred at 60° C. for 18 hrs and cooled to room temperature. Diethyl ether was added and the resulting precipitate was filtered and washed with ether three times to give 1-(4-nitrophenyl)-N,N,N-trimethylpyrrolidin-3-aminium iodide (894 mg, 92% yield): $^1$HNMR (400 MHz, DMSO-$d_6$)δ 2.50 (m, 2H), 3.15 (s, 9H), 3.43 (m, 1H), 3.71 (m, 2H), 3.87 (m, 1H), 4.37 (m, 1H), 6.74 (d, 2H, J=9 Hz), 8.12(d, 2H, J=9 Hz). This compound was hydrogenated at 60 psi in menthol in the presence of 10% Pd/C at room temperature for about 18 hrs. The reaction mixture was filtered through a pad of Celite and washed with methanol. The filtrate was evaporated in vacuo to produce 1-(4-aminophenyl)-N,N,N-trimethylpyrrolidin-3-aminium iodide (505 mg, 95% yield): $^1$HNMR (400 MHz, DMSO-$d_6$)δ 2.32 (m, 2H), 2.94 (m, 1H), 3.09 (s, 9H), 3.17 (m, 2H), 3.71 (m, 2H), 4.25 (m, 1H), 4.66 (bs, 2H), 6.52 (s, 4H): MS m/z=219. This is Compound 1 of Table 1.

Examples 2 to 15

With the substitution of the appropriate R-X reactant for methyl iodide in the synthesis procedure of Example 1 Compounds 2 to 15 of Table 1 were prepared.

TABLE 1

| Ex. No. | Compound | R | $R^1$ | $R^2$ | $R^3$ | $R^4$ | $R^5$ | X |
|---|---|---|---|---|---|---|---|---|
| 1 | 1 | $CH_3$ | $CH_3$ | $CH_3$ | | H | H | I |
| 2 | 2 | $C_2H_5$ | $CH_3$ | $CH_3$ | | H | H | I |
| 3 | 3 | $C_3H_7$ | $CH_3$ | $CH_3$ | | H | H | I |
| 4 | 4 | $C_3H_7$ | $CH_3$ | $CH_3$ | $C_3H_7$ | H | H | $R^3SO_4$ |
| 5 | 5 | $C_3H_7$ | $CH_3$ | $CH_3$ | | H | H | Br |
| 6 | 6 | $C_4H_9$ | $CH_3$ | $CH_3$ | | H | H | I |
| 7 | 7 | $C_5H_{11}$ | $CH_3$ | $CH_3$ | | H | H | I |
| 8 | 8 | $C_6H_{13}$ | $CH_3$ | $CH_3$ | | H | H | I |
| 9 | 9 | $C_7H_{15}$ | $CH_3$ | $CH_3$ | | H | H | I |
| 10 | 10 | $C_8H_{17}$ | $CH_3$ | $CH_3$ | | H | H | I |
| 11 | 11 | $C_9H_{19}$ | $CH_3$ | $CH_3$ | | H | H | I |
| 12 | 12 | $C_{10}H_{21}$ | $CH_3$ | $CH_3$ | | H | H | I |
| 13 | 13 | $C_{16}H_{33}$ | $CH_3$ | $CH_3$ | | H | H | I |
| 14 | 14 | $C_2H_4OH$ | $CH_3$ | $CH_3$ | | H | H | I |
| 15 | 15 | $C_2H_4OH$ | $CH_3$ | $CH_3$ | | H | H | Br |

Dyeing Tests

Examples 16 to 45

Hair Coloring Compositions and Hair Dyeing Therewith

Hair coloring compositions 16 to 45 of this invention were prepared and tested employing the quaternized pyrrolidine primary intermediate compounds of Examples 1 to 15 as listed in Table 1, and the coupler compounds as indicated in Tables 2 and 3. Piedmont hair weighing from 700 to 900 mg was used. A solution of the primary intermediate compound and each coupler was prepared separately according to the following procedure. The concentration of the primary intermediate and the coupler was 0.025 M in a base consisting of cocamidopropyl betaine 17 g, monoethanol amine 2 g, oleic acid 0.75 g, citric acid 0.1 g, ammonium hydroxide (28%) 5 g, behentrimonium chloride 0.5 g and water to 100 g. A solution of 0.5 mL primary intermediate and 0.5 mL coupler was mixed with 20 volumes hydrogen peroxide (1 mL). The mixture was applied to Piedment hair tresses mounted on a glass plate and then stored at 40° C. for 30 minutes, washed, shampooed, and dried. evaluated using the Minolta Spectrophotometer CM-3700d The Minolta 3700d spectrophotometer uses reflected light from a surface and gives results in terms of the CIE (International Commission on Illumination) tristimulus values. These values are subsequently transformed mathematically into the L* a* b* color space, wherein the magnitude of changes in hue and intensity of color correspond closely with those perceived by the human eye. L*, being achromatic, ranges from black (L*=0) to white (L*=100); this term is called "metric lightness" and is a measure of how light or dark a color is, relative to a matching shade of gray. Hue is measured in terms of the chromaticity coordinates a* and b*, where a* indicates redness (a*>0) and b* indicates yellowness (b*>0). The values of a* and b* can be plotted with a* as the x-axis and b* as the y-axis to give quantitative color information: "metric chroma" is the length of a line from the origin (a*=0, b*=0) to the point of a sample reading while metric hue angle is the angle between the a* axis and the metric chroma line. Metric chroma indicates the strength of a color response (i.e., the extent to which a color differs from its matching shade of gray). Metric hue angle quantifies hue in degrees, with larger values indicating more yellow hues and smaller values indicating more red (or less yellow) hues.

The results of the tests are set forth in the following Tables 2 and 3. The baseline average values of L*, a* and b* for undyed, untreated Piedmont hair were L* 72.32, a* 2.0, b* 23.2.

TABLE 2

Compounds synthesized and their dyeing results with various couplers

| Example | Compound | Structure | IUPAC | Resorcinol | | | m-Aminophenol | | | AMP* | | | DAP* | | |
|---|---|---|---|---|---|---|---|---|---|---|---|---|---|---|---|
| | | | | L* | a* | b* | L* | a* | b* | L* | a* | b* | L* | a* | b* |
| 16 | 1 | [structure] | 1-(4-aminophenyl)-N,N,N-trimethylpyrrolidin-3-aminium iodide | 46.14 | 4.66 | 6.4 | | | | 31.11 | 14.94 | −11.49 | 39.36 | 1.48 | −17.21 |
| 17 | 2 | [structure] | 1-(4-aminophenyl)-N-ethyl-N,N-dimethylpyrrolidin-3-aminium iodide | 43.44 | 4.34 | 8.35 | 31.24 | 3.5 | −8.09 | 34.83 | 11.59 | −8.84 | 28.5 | 0.839 | −14.72 |

TABLE 2-continued

Compounds synthesized and their dyeing results with various couplers

| Example | Compound | Structure | IUPAC | Resorcinol | | | m-Aminophenol | | | AMP* | | | DAP* | | |
|---|---|---|---|---|---|---|---|---|---|---|---|---|---|---|---|
| | | | | L* | a* | b* | L* | a* | b* | L* | a* | b* | L* | a* | b* |
| 18 | 3 | | 1-(4-aminophenyl)-N,N-dimethyl-N-propylpyrrolidin-3-aminium iodide | 50.83 | 4 | 8.13 | | | | 35.26 | 13.84 | 9.94 | 38.49 | −2.23 | −12.46 |
| 19 | 4 | | 1-(4-aminophenyl)-N,N-dimethyl-N-propylpyrrolidin-3-aminium propyl sulfate | 43.93 | 3.34 | 10.98 | | | | 38.81 | 12.14 | −7.02 | 28.13 | 1.31 | 17.3 |

TABLE 2-continued
Compounds synthesized and their dyeing results with various couplers
| | | | | Couplers | | | | | | | | | | |
|---|---|---|---|---|---|---|---|---|---|---|---|---|---|---|
| | | | Resorcinol | | | m-Aminophenol | | | AMP* | | | DAP* | | |
| Example | Compound | Structure | IUPAC | L* | a* | b* | L* | a* | b* | L* | a* | b* | L* | a* | b* |
| 20 | 5 | 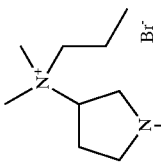 | 1-(4-aminophenyl)-N,N-dimethyl-N-propylpyrrolidin-3-aminium bromide | 44.98 | 3.57 | 11.01 | | | | 36.01 | 14.1 | −6.36 | 28.95 | 0.86 | −16.74 |
| 21 | 6 | 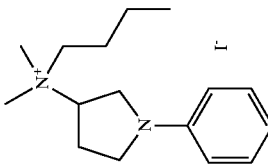 | 1-(4-aminophenyl)-N,N-dimethyl-N-butylpyrrolidin-3-aminium iodide | 43.8 | 3.09 | 8.55 | 36.16 | 3.56 | −4.5 | 39.87 | 10.74 | −2.97 | 29.45 | 1.37 | −12.29 |

TABLE 2-continued

Compounds synthesized and their dyeing results with various couplers

| Example | Compound | Structure | IUPAC | Resorcinol | | | m-Aminophenol | | | AMP* | | | DAP* | | |
|---|---|---|---|---|---|---|---|---|---|---|---|---|---|---|---|
| | | | | L* | a* | b* | L* | a* | b* | L* | a* | b* | L* | a* | b* |
| 22 | 7 | 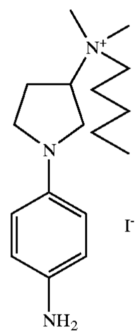 | 1-(4-aminophenyl)-N,N-dimethyl-N-pentylpyrrolidin-3-aminium iodide | 46.02 | 3.21 | 7.17 | | | | | | | 30.25 | 0.5 | −15.08 |
| 23 | 8 | 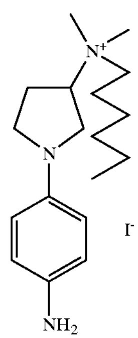 | 1-(4-aminophenyl)-N-hexyl-N,N-dimethylpyrrolidin-3-aminium iodide | 48.12 | 3.36 | 10.83 | 42.16 | 4.17 | 1 | 47.76 | 8.06 | 2.18 | 32.1 | 2.46 | −10.56 |

TABLE 2-continued
Compounds synthesized and their dyeing results with various couplers
| Example | Compound | Structure | IUPAC | Couplers | | | | | | | | | | | | |
|---|---|---|---|---|---|---|---|---|---|---|---|---|---|---|---|---|
| | | | | Resorcinol | | | m-Aminophenol | | | AMP* | | | DAP* | | |
| | | | | $L^*$ | $a^*$ | $b^*$ | $L^*$ | $a^*$ | $b^*$ | $L^*$ | $a^*$ | $b^*$ | $L^*$ | $a^*$ | $b^*$ |
| 24 | 9 | 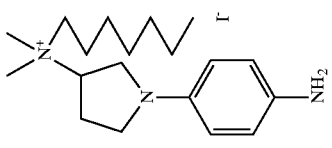 | 1-(4-aminophenyl)-N-heptyl-N,N-dimethylpyrrolidin-3-aminium iodide | 50.79 | 2.78 | 11.05 | 42.32 | 2.77 | 2.27 | 48.4 | 6.51 | 3.24 | 36.76 | 2.05 | -8.21 |
| 25 | 10 | 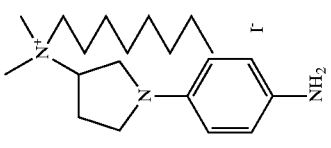 | 1-(4-aminophenyl)-N,N-dimethyl-N-octylpyrrolidin-3-aminium iodide | 51.96 | 2.17 | 10.35 | 48.09 | 2.95 | 4.63 | 52.1 | 5.98 | 6.27 | 34.5 | 3.52 | -8.18 |

TABLE 2-continued

Compounds synthesized and their dyeing results with various couplers

| Example | Compound | Structure | IUPAC | Couplers | | | | | | | | | | | |
|---|---|---|---|---|---|---|---|---|---|---|---|---|---|---|---|
| | | | | Resorcinol | | | m-Aminophenol | | | AMP* | | | DAP* | | |
| | | | | L* | a* | b* | L* | a* | b* | L* | a* | b* | L* | a* | b* |
| 26 | 11 | | 1-(4-aminophenyl)-N,N-dimethyl-N-nonylpyrrolidin-3-aminium iodide | 56.39 | 1.58 | 12.57 | 51.12 | 1.7 | 6.24 | 54.38 | 3.92 | 6.03 | 33.01 | 2.32 | -6.71 |
| 27 | 12 | | 1-(4-aminophenyl)-N-decyl-N,N-dimethylpyrrolidin-3-aminium iodide | 51.81 | 3.02 | 10.43 | | | | 49.31 | 9.56 | -3.08 | 32.4 | 1.2 | -15.96 |

TABLE 2-continued

Compounds synthesized and their dyeing results with various couplers

| Example | Compound | Structure | IUPAC | Resorcinol | | | m-Aminophenol | | | AMP* | | | DAP* | | |
|---|---|---|---|---|---|---|---|---|---|---|---|---|---|---|---|
| | | | | L* | a* | b* | L* | a* | b* | L* | a* | b* | L* | a* | b* |
| 28 | 13 | 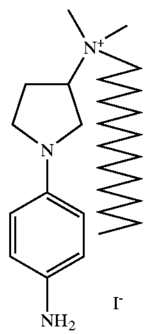 | 1-(4-aminophenyl)-N-hexadecyl-N,N-dimethylpyrrolidin-3-aminium iodide | 65.73 | 2.41 | 14.39 | | | | 62.08 | 5.9 | 5.93 | 48.58 | −3.74 | −7.17 |
| 29 | 14 | 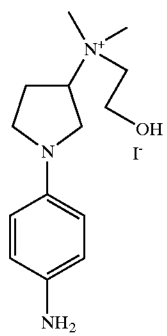 | 1-(4-aminophenyl)-N-(2-hydroxyethyl)-N,N-dimethylpyrrolidin-3-aminium iodide | 46.32 | 3.69 | 8.23 | 32.17 | 4.26 | −8.45 | 38.24 | 11.77 | −8.28 | 32.15 | −0.2 | −14.67 |

TABLE 2-continued

Compounds synthesized and their dyeing results with various couplers

| | | | | Couplers | | | | | | | | | |
|---|---|---|---|---|---|---|---|---|---|---|---|---|---|
| | | | | Resorcinol | | | m-Aminophenol | | | AMP* | | | DAP* |
| Example | Compound | Structure | IUPAC | L* | a* | b* | L* | a* | b* | L* | a* | b* | L* | a* | b* |
| 30 | 15 | [structure] | 1-(4-aminophenyl)-N-(2-hydroxyethyl)-N,N-dimethylpyrrolidin-3-aminium bromide | 42.76 | 3.16 | 10.37 | 37.66 | 3.88 | −1.7 | 47.4 | 8.4 | 1.28 | 33.26 | 0.16 | −16.47 |

AMP: 5-Amino-2-methylphenol
DAP: 2,4-Diaminophenoxyethanol

TABLE 3

Colors obtained by coupling

| Example | Compound | Coupler | Color |
|---|---|---|---|
| 31 | 1 | Benzene-1,3-diol | greenish yellow |
| | 1 | 3-Amino-phenol | blue violet |
| | 1 | 5-Amino-2-methyl-phenol | violet |
| | 1 | 2-(2,4-Diamino-phenoxy)-ethanol | blue |
| 32 | 2 | Benzene-1,3-diol | greenish yellow |
| | 2 | 3-Amino-phenol | blue violet |
| | 2 | 5-Amino-2-methyl-phenol | violet |
| | 2 | 2-(2,4-Diamino-phenoxy)-ethanol | blue |
| 33 | 3 | Benzene-1,3-diol | greenish yellow |
| | 3 | 3-Amino-phenol | blue violet |
| | 3 | 5-Amino-2-methyl-phenol | violet |
| | 3 | 2-(2,4-Diamino-phenoxy)-ethanol | blue |
| 34 | 4 | Benzene-1,3-diol | greenish yellow |
| | 4 | 3-Amino-phenol | blue violet |
| | 4 | 5-Amino-2-methyl-phenol | violet |
| | 4 | 2-(2,4-Diamino-phenoxy)-ethanol | blue |
| 35 | 5 | Benzene-1,3-diol | greenish yellow |
| | 5 | 3-Amino-phenol | blue violet |
| | 5 | 5-Amino-2-methyl-phenol | violet |
| | 5 | 2-(2,4-Diamino-phenoxy)-ethanol | blue |
| 36 | 6 | Benzene-1,3-diol | greenish yellow |
| | 6 | 3-Amino-phenol | blue violet |
| | 6 | 5-Amino-2-methyl-phenol | violet |
| | 6 | 2-(2,4-Diamino-phenoxy)-ethanol | blue |
| 37 | 7 | Benzene-1,3-diol | greenish yellow |
| | 7 | 3-Amino-phenol | blue violet |
| | 7 | 5-Amino-2-methyl-phenol | violet |
| | 7 | 2-(2,4-Diamino-phenoxy)-ethanol | blue |
| 38 | 8 | Benzene-1,3-diol | greenish yellow |
| | 8 | 3-Amino-phenol | blue violet |
| | 8 | 5-Amino-2-methyl-phenol | violet |
| | 8 | 2-(2,4-Diamino-phenoxy)-ethanol | blue |
| 39 | 9 | Benzene-1,3-diol | greenish yellow |
| | 9 | 3-Amino-phenol | blue violet |
| | 9 | 5-Amino-2-methyl-phenol | violet |
| | 9 | 2-(2,4-Diamino-phenoxy)-ethanol | blue |
| 40 | 10 | Benzene-1,3-diol | greenish yellow |
| | 10 | 3-Amino-phenol | blue violet |
| | 10 | 5-Amino-2-methyl-phenol | violet |
| | 10 | 2-(2,4-Diamino-phenoxy)-ethanol | blue |
| 41 | 11 | Benzene-1,3-diol | greenish yellow |
| | 11 | 3-Amino-phenol | blue violet |
| | 11 | 5-Amino-2-methyl-phenol | violet |
| | 11 | 2-(2,4-Diamino-phenoxy)-ethanol | blue |
| 42 | 12 | Benzene-1,3-diol | greenish yellow |
| | 12 | 3-Amino-phenol | blue violet |
| | 12 | 5-Amino-2-methyl-phenol | violet |
| | 12 | 2-(2,4-Diamino-phenoxy)-ethanol | blue |
| 43 | 13 | Benzene-1,3-diol | greenish yellow |
| | 13 | 3-Amino-phenol | blue violet |
| | 13 | 5-Amino-2-methyl-phenol | violet |
| | 13 | 2-(2,4-Diamino-phenoxy)-ethanol | blue |
| 44 | 14 | Benzene-1,3-diol | greenish yellow |
| | 14 | 3-Amino-phenol | blue violet |
| | 14 | 5-Amino-2-methyl-phenol | violet |
| | 14 | 2-(2,4-Diamino-phenoxy)-ethanol | blue |
| 45 | 15 | Benzene-1,3-diol | greenish yellow |
| | 15 | 3-Amino-phenol | blue violet |
| | 15 | 5-Amino-2-methyl-phenol | violet |
| | 15 | 2-(2,4-Diamino-phenoxy)-ethanol | blue |

Synthesis Examples 46 and 47

Employing the procedure as set forth in Example 1, but employing the appropriate amount of methyl chloride or methyl sulfate reactant in place of methyl iodide, there is prepared [1-(4-aminophenyl)-pyrrolidin-yl]-trimethyl ammonium chloride or [1-(4-aminophenyl)-pyrrolidin-yl]-trimethyl ammoniun sulfate.

The compounds of this invention show substantially less sensitization potential than non-quaternized compounds and p-phenylenediamine. For example, the compound of Example 1 and the [1-(4-aminophenyl)-pyrrolidin-yl]-trimethyl ammoniun sulfate compound of Example 47 showed substantially less sensitization (allergy) potential in the Local Lymph Node Assay. The assay is described in Contact Dermatitis 42(6), 344–348, June 2000.

Preferred combinations of hair coloring components employing a quaternized pyrrolidine primary intermediate of this invention are shown in combinations C1 to C116 in Tables A through G. Reading down the columns in Table A, the Xes designate combinations of dyes that can be formulated according to the present invention. For example, in Example No. C1 of Table A, a quaternized pyrrolidine compound of formula (1) of this invention (Row 1 of Table A) can be combined with 2-amino-phenol (Row 7 of Table A) and in Example C3 of Table A, a quaternized pyrrolidine compound of formula (1) of this invention (Row 1 of Table A) can be combined with 2-methyl-benzene-1,3-diol (Row 9 of Table A). Especially preferred as compounds of the formula (I) component in the combinations C1 to C116 of Table are 1-(4-aminophenyl)-N,N-dimethyl-N-propyllpyrrolidin-3-aminium bromide and 1-(4-aminophenyl)-N,N-dimethyl-N-propylpyrrolidin-3-aminium propyl sulfate, although any quaternized pyrrolidine compound of this invention may be employed.

TABLE A

Dye Combinations

| Structure | IUPAC Name | Name | C1 | C2 | C3 | C4 | C5 | C6 | C7 | C8 | C9 | C10 | C11 |
|---|---|---|---|---|---|---|---|---|---|---|---|---|---|
| (structure) | [1-(4-Amino-phenyl)-pyrrolidin-yl]-trialkyl-ammonium halide (sulfate) | | x | x | x | x | x | x | x | x | x | x | x |
| (structure) | 2-Methyl-benzene-1,4-diamine | p-Toluene-diamine | | | | | | | | | | | |
| (structure) | Benzene-1,4-diamine | p-Phenylene-diamine | | | | | | | | | | | |
| (structure) | 2-[(4-Amino-phenyl)-(2-hydroxy-ethyl)-amino]-ethanol | N,N-Bis(2-hydroxy-ethyl)-p-phenylene-diamine | | | | | | | | | | | |
| (structure) | 4-Amino-phenol | p-Aminophenol | | | | | | | | | | x | x |
| (structure) | 4-Amino-3-methyl-phenol | 3-Methyl-p-aminophenol | | | | | | | | | | | |
| (structure) | 2-Amino-phenol | o-Aminophenol | x | | | | | | | | | x | |
| (structure) | Benzene-1,3-diol | Resorcinol | | | x | | | | | | | | x |
| (structure) | 2-Methyl-benzene-1,3-diol | 2-Methyl-resorcinol | | | | x | | | | | | | |
| (structure) | Naphthalen-1-ol | 1-Naphthol | | | | | x | | | | | | |
| (structure) | 2-Methyl-naphthalen-1-ol | 2-Methyl-1-naphthol | | | | | | x | | | | | |

TABLE A-continued

Dye Combinations

| Structure | IUPAC Name | Name | C1 | C2 | C3 | C4 | C5 | C6 | C7 | C8 | C9 | C10 | C11 |
|---|---|---|---|---|---|---|---|---|---|---|---|---|---|
| 2,4-diamino-phenol with OCH₂CH₂OH (structure: H$_2$N-C$_6$H$_3$(NH$_2$)-OCH$_2$CH$_2$OH) | 2-(2,4-Diamino-phenoxy)-ethanol | 2,4-Diamino-phenoxyethanol | | | | | | x | | | | | |
| Benzene with two NH$_2$ groups in 1,3-positions | Benzene-1,3-diamine | m-Phenylene-diamine | | | | | | | | x | | | |
| 3-aminophenol (HO- and -NH$_2$ on benzene in meta positions) | 3-Amino-phenol | m-Aminophenol | | | | | | | | | x | | |
| 5-amino-2-methylphenol (benzene with CH$_3$, OH, and H$_2$N substituents) | 5-Amino-2-methyl-phenol | 2-Hydroxy-4-aminotoluene | | | | | | | | | | x | |
| 4,5-diamino-1-(2-hydroxyethyl)pyrazole | 2-(4,5-Diamino-pyrazol-1-yl)-ethanol | 1-Hydroxyethyl-4,5-diamino-pyrazole | | | | | | | | | | | |

TABLE B

Dye Combinations

| Structure | C12 | C13 | C14 | C15 | C16 | C17 | C18 | C19 | C20 |
|---|---|---|---|---|---|---|---|---|---|
| Pyrrolidine derivative: RR'R''N$^+$X$^-$ attached to pyrrolidine-N-phenyl-NH$_2$ | x | x | x | x | x | x | x | x | x |
| 2-methyl-1,4-diaminobenzene (H$_2$N-C$_6$H$_3$(CH$_3$)-NH$_2$) | | | | | | | | | |
| 1,4-diaminobenzene (H$_2$N-C$_6$H$_4$-NH$_2$) | | | | | | | | | |
| H$_2$N-C$_6$H$_4$-N(CH$_2$CH$_2$OH)$_2$ | | | | | | | | | |
| 4-aminophenol (HO-C$_6$H$_4$-NH$_2$) | x | x | x | x | x | x | x | | |

TABLE B-continued
Dye Combinations
| Structure | | | | | | |
|---|---|---|---|---|---|---|
| 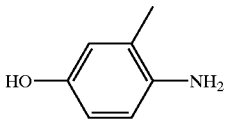 4-hydroxy-2-methylaniline | | | | | x | x |
| 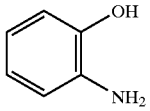 2-aminophenol | | | | | | x |
| 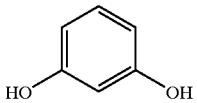 resorcinol | | | | | | x |
| 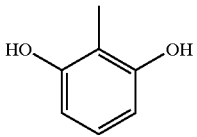 2-methylresorcinol | x | | | | | |
| 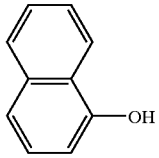 1-naphthol | x | | | | | |
| 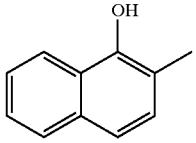 2-methyl-1-naphthol | | x | | | | |
| 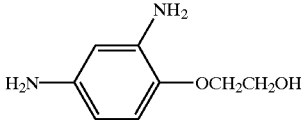 2-amino-4-(2-hydroxyethoxy)aniline | | x | | | | |
| 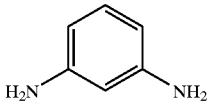 m-phenylenediamine | | | x | | | |
| 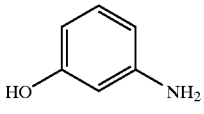 3-aminophenol | | | | x | | |
| 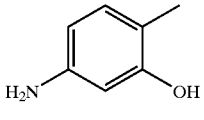 5-amino-2-methylphenol | | | | | x | |
| 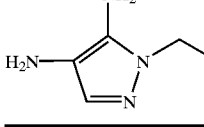 4,5-diamino-1-(2-hydroxyethyl)pyrazole | | | | | | |

TABLE B-continued

Dye Combinations

| Structure | C21 | C22 | C23 | C24 | C25 | C26 | C27 | C28 | C29 |
|---|---|---|---|---|---|---|---|---|---|
| [pyrrolidine-aniline quaternary ammonium structure] | x | x | x | x | x | x | x | x | x |
| 2-methyl-1,4-diaminobenzene | | | | | | | | | |
| 1,4-diaminobenzene | | | | | | | | | |
| $H_2N$–C$_6$H$_4$–$N(CH_2CH_2OH)_2$ | | | | | | | | | |
| 4-aminophenol | | | | | | | | | |
| 4-amino-3-methylphenol | x | x | x | x | x | x | x | | |
| 2-aminophenol | | | | | | | | | |
| resorcinol | | | | | | | | x | x |
| 2-methylresorcinol | | x | | | | | x | | |
| 1-naphthol | | | x | | | | | | x |
| 2-methyl-1-naphthol | | | | x | | | | | |

TABLE B-continued

Dye Combinations

| Structure | |
|---|---|
| 2,4-diamino-phenoxyethanol | x (column position) |
| m-phenylenediamine | x |
| 3-aminophenol | x |
| 5-amino-2-methylphenol | x |
| 4,5-diamino-1-(2-hydroxyethyl)pyrazole | |

TABLE C

Dye Combinations

| Structure | C30 | C31 | C32 | C33 | C34 | C35 | C36 | C37 | C38 |
|---|---|---|---|---|---|---|---|---|---|
| pyrrolidine-aniline quaternary | x | x | x | x | x | x | x | x | x |
| 2-methyl-1,4-phenylenediamine | | | | | | x | x | x | x |
| 1,4-phenylenediamine | | | | | | | | | |
| N,N-bis(2-hydroxyethyl)-p-phenylenediamine | | | | | | | | | |
| 4-aminophenol | | | | | | | | | |
| 2-methyl-4-aminophenol | | | | | | | | | |

TABLE C-continued

Dye Combinations

| Structure | C39 | C40 | C41 | C42 | C43 | C44 | C45 | C46 | C47 |
|---|---|---|---|---|---|---|---|---|---|
| 2-aminophenol (OH, NH$_2$) | | | | | | x | | | |
| resorcinol (1,3-dihydroxybenzene) | x | x | x | x | x | x | x | x | x |
| 2-methylresorcinol | | | | | | | x | | |
| 1-naphthol | | | | | | | x | | |
| 2-methyl-1-naphthol | x | | | | | | | | x |
| 2,4-diamino-phenoxyethanol | | | x | | | | | | |
| m-phenylenediamine | | | | x | | | | | |
| 3-aminophenol | | | | | x | | | | |
| 5-amino-2-methylphenol | | | | | x | | | | |
| 4,5-diamino-1-(2-hydroxyethyl)pyrazole | | | | | | | | | |
| pyrrolidinyl-phenylamine ammonium salt | x | x | x | x | x | x | x | x | x |

TABLE C-continued

Dye Combinations

| Structure | 1 | 2 | 3 | 4 | 5 | 6 | 7 | 8 | 9 | 10 |
|---|---|---|---|---|---|---|---|---|---|---|
| $H_2N$-(2-methyl-1,4-phenylene)-$NH_2$ | x | x | x | x | | | | | | |
| $H_2N$-(1,4-phenylene)-$NH_2$ | | | | | x | x | x | x | x | |
| $H_2N$-(1,4-phenylene)-$N(CH_2CH_2OH)_2$ | | | | | | | | | | |
| $HO$-(1,4-phenylene)-$NH_2$ | | | | | | | | | | |
| $HO$-(2-methyl-4-amino-phenyl) | | | | | | | | | | |
| 2-aminophenol ($OH$, $NH_2$) | | | | | | x | | | | |
| resorcinol ($HO$, $OH$) | | x | x | x | x | x | x | x | x | x |
| 2-methylresorcinol | | | | | | | x | | | |
| 1-naphthol | | | | | | | x | | | |
| 2-methyl-1-naphthol | | | | | | | | | x | |
| 2-amino-4-(2-hydroxyethoxy)aniline | | | x | | | | | | | x |

TABLE C-continued
Dye Combinations
| Structure | | | | | | | | | |
|---|---|---|---|---|---|---|---|---|---|
| 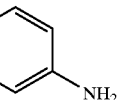 | | x | | | | | | | |
| 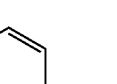 | | | x | | | | | | |
| 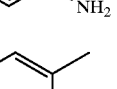 | | | | x | | | | | |
| 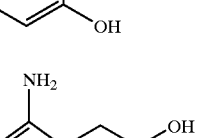 | | | | | | | | | |
TABLE D
Dye Combinations
| Structure | C48 | C49 | C50 | C51 | C52 | C53 | C54 | C55 | C56 |
|---|---|---|---|---|---|---|---|---|---|
| (structure with pyrrolidine, NR'R''R, X⁻, and -NH₂) | x | x | x | x | x | x | x | x | x |
| (2-methyl-1,4-diaminobenzene) | | | | | | | | | |
| (1,4-diaminobenzene) | | x | x | x | | | | | |
| H₂N—C₆H₄—N(CH₂CH₂OH)₂ | | | | | | | | | |
| HO—C₆H₄—NH₂ | | | | x | x | x | x | x | x |
| (3-methyl-4-aminophenol) | | | | | | | | | |
| (2-aminophenol) | | | | | | | | | |

TABLE D-continued

Dye Combinations

| Structure | C57 | C58 | C59 | C60 | C61 | C62 | C63 | C64 | C65 |
|---|---|---|---|---|---|---|---|---|---|
| resorcinol (HO-C6H4-OH, 1,3) | x | x | x | x | x | x | x | x | x |
| 2-methylresorcinol | | | | | x | | | | |
| 1-naphthol | | | | | | x | | | |
| 2-methyl-1-naphthol | | | | | | | x | | |
| 2,4-diamino-1-(2-hydroxyethoxy)benzene | | | | | | | | x | |
| 1,3-diaminobenzene | | x | | | | | | | x |
| 3-aminophenol | | | x | | | | | | |
| 5-amino-2-methylphenol | | | x | | | | | | |
| 4,5-diamino-1-(2-hydroxyethyl)pyrazole | | | | | | | | | |

| Structure | C57 | C58 | C59 | C60 | C61 | C62 | C63 | C64 | C65 |
|---|---|---|---|---|---|---|---|---|---|
| pyrrolidinyl-aniline ammonium (R, R', R'', X⁻) | x | x | x | x | x | x | x | x | x |

TABLE D-continued

Dye Combinations

| Structure | | | | | | | | | |
|---|---|---|---|---|---|---|---|---|---|
| 2-methyl-1,4-diaminobenzene (H₂N-C₆H₃(CH₃)-NH₂) | | | | | | | | | |
| 1,4-diaminobenzene (H₂N-C₆H₄-NH₂) | | | | | | | | | |
| H₂N-C₆H₄-N(CH₂CH₂OH)₂ | | | | | | | | | |
| HO-C₆H₄-NH₂ (4-aminophenol) | x | x | | | | | | | |
| HO-C₆H₃(CH₃)-NH₂ (2-methyl-4-aminophenol) | | | x | x | x | x | x | x | x |
| 2-aminophenol (OH, NH₂ ortho) | | | x | | | | | | |
| resorcinol (HO-C₆H₄-OH, 1,3) | x | x | x | x | x | x | x | x | x |
| 2-methylresorcinol | | | | x | | | | | |
| 1-naphthol | | | | | x | | | | |
| 2-methyl-1-naphthol | | | | | | | x | | |
| 2,4-diamino-1-(2-hydroxyethoxy)benzene (H₂N-C₆H₃(NH₂)-OCH₂CH₂OH) | | | | | | | | x | |
| 1,3-diaminobenzene (H₂N-C₆H₄-NH₂, meta) | | | | | | | | | x |

TABLE D-continued

Dye Combinations

| Structure | | | | | | | | | |
|---|---|---|---|---|---|---|---|---|---|
| HO-C6H4-NH2 (3-aminophenol) | | x | | | | | | | x |
| H2N-C6H3(CH3)-OH (5-amino-2-methylphenol) | | | x | | | | | | |
| 4,5-diamino-1-(2-hydroxyethyl)pyrazole | | | | | | | | | |

TABLE E

Dye Combinations

| Structure | C66 | C67 | C68 | C69 | C70 | C71 | C72 | C73 | C74 |
|---|---|---|---|---|---|---|---|---|---|
| R,R',R''-N-pyrrolidine-C6H4-NH2, X⁻ | x | x | x | x | x | x | x | x | x |
| 2-methyl-1,4-phenylenediamine | | | | | | | | | |
| 1,4-phenylenediamine | | | | | | | | | |
| H2N-C6H4-N(CH2CH2OH)2 | | x | x | x | x | x | x | x | x |
| HO-C6H4-NH2 (4-aminophenol) | | | | | | | | | |
| 2-amino-5-methylphenol | | x | | | | | | | |
| 2-aminophenol | | | | | | | | | |
| resorcinol | | x | x | | | | | | |

TABLE E-continued

Dye Combinations

| Structure | | | | | | | | | |
|---|---|---|---|---|---|---|---|---|---|
| 2-methylresorcinol (HO-C₆H₃(CH₃)-OH) | | | x | | | | | | |
| 1-naphthol | | | | | x | | | | |
| 2-methyl-1-naphthol | | | | | | x | | | |
| 2,4-diamino-1-(2-hydroxyethoxy)benzene | | | | | | | x | | |
| m-phenylenediamine | | | | | | | | x | |
| 3-aminophenol | | | | | | | | | x |
| 5-amino-2-methylphenol | x | | | | | | | | x |

| Structure | C75 | C76 | C77 | C78 | C79 | C80 | C81 | C82 | C83 |
|---|---|---|---|---|---|---|---|---|---|
| pyrrolidinium-phenylamine (R,R',R'' substituted, X⁻) | x | x | x | x | x | x | x | x | x |
| 2-methyl-p-phenylenediamine | | | | | | | | | |
| p-phenylenediamine | | | | | | | | | |

TABLE E-continued

Dye Combinations

| Structure | 1 | 2 | 3 | 4 | 5 | 6 | 7 | 8 | 9 |
|---|---|---|---|---|---|---|---|---|---|
| $H_2N$-C$_6$H$_4$-N(CH$_2$CH$_2$OH)$_2$ | | | | | | | | | |
| HO-C$_6$H$_4$-NH$_2$ (4-aminophenol) | x | x | x | x | x | x | x | x | x |
| HO-C$_6$H$_3$(CH$_3$)-NH$_2$ | | | | | | | | | |
| 2-aminophenol (OH, NH$_2$ ortho) | x | | | | | | | | |
| Resorcinol (1,3-dihydroxybenzene) | | x | | | | | | | |
| 2-methylresorcinol | | | x | | | | | | |
| 1-naphthol | | | | x | | | | | |
| 2-methyl-1-naphthol | | | | | x | | | | |
| 2,4-diamino-1-(2-hydroxyethoxy)benzene | | | | | x | | | | |
| 1,3-diaminobenzene | | | | | | | x | | |
| 3-aminophenol | | | | | | | | x | |

TABLE E-continued

Dye Combinations

| Structure | | | | | | | | | |
|---|---|---|---|---|---|---|---|---|---|
| 5-amino-2-methylphenol (H₂N–C₆H₃(CH₃)–OH) | | | | | | | | | x |
| 4,5-diamino-1-(2-hydroxyethyl)pyrazole | x | x | x | x | x | x | x | x | x |

TABLE F

Dye Combinations

| Structure | C84 | C85 | C86 | C87 | C88 | C89 | C90 | C91 | C92 |
|---|---|---|---|---|---|---|---|---|---|
| R,R',R''-N-pyrrolidinyl-(4-aminophenyl) X⁻ | x | x | x | x | x | x | x | x | x |
| 2-methyl-1,4-phenylenediamine | | | | | | | | | |
| 1,4-phenylenediamine | | | | | | | | | |
| N,N-bis(2-hydroxyethyl)-1,4-phenylenediamine | | | | | | | | | |
| 4-aminophenol | | | | | | | | | |
| 4-amino-3-methylphenol | x | x | x | x | x | x | x | x | x |
| 2-aminophenol | | x | | | | | | | |
| resorcinol | | | x | | | | | | |
| 2-methylresorcinol | | | | x | | | | | |

TABLE F-continued
Dye Combinations
| Structure | | | | | | | | | |
|---|---|---|---|---|---|---|---|---|---|
| 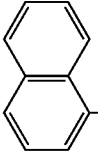 (1-naphthol) | | | x | | | | | | |
| 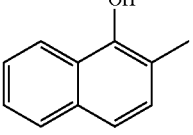 (2-methyl-1-naphthol) | | | | x | | | | | |
| 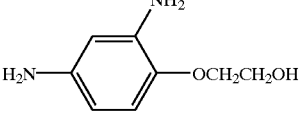 (2,4-diamino-1-(2-hydroxyethoxy)benzene) | | | | | x | | | | |
| 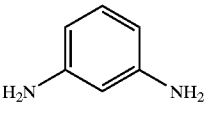 (m-phenylenediamine) | | | | | | x | | | |
| 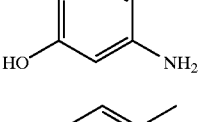 (3-aminophenol) | | | | | | | x | | |
| 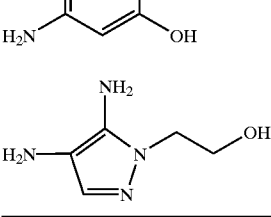 (5-amino-2-methylphenol) | | | | | | | | x | |
| 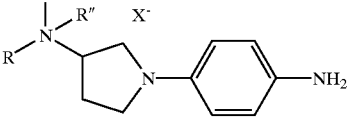 (4,5-diamino-1-(2-hydroxyethyl)pyrazole) | x | x | x | x | x | x | x | x | x |
| Structure | C93 | C94 | C95 | C96 | C97 | C98 | C99 | C100 | C101 |
|---|---|---|---|---|---|---|---|---|---|
| 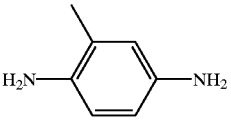 | x | x | x | x | x | x | x | x | x |
| 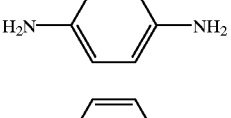 (2-methyl-p-phenylenediamine) | x | x | x | x | x | x | x | x | |
|  (p-phenylenediamine) | | | | | | | | | x |
| $H_2N$-⟨⟩-$N(CH_2CH_2OH)_2$ | | | | | | | | | |

TABLE F-continued

Dye Combinations

| Structure | | | |
|---|---|---|---|
| HO—C$_6$H$_4$—NH$_2$ (4-aminophenol) | | | |
| HO—C$_6$H$_3$(CH$_3$)—NH$_2$ (methyl aminophenol) | | | |
| 2-aminophenol (OH, NH$_2$ ortho) | | | |
| resorcinol (HO—C$_6$H$_4$—OH, 1,3) | x | | x |
| 2-methylresorcinol | | x | |
| 1-naphthol | | x | |
| 2-methyl-1-naphthol | | | x |
| 2,4-diamino-1-(2-hydroxyethoxy)benzene (H$_2$N—C$_6$H$_3$(NH$_2$)—OCH$_2$CH$_2$OH) | | | x |
| m-phenylenediamine (H$_2$N—C$_6$H$_4$—NH$_2$) | | | x |
| 3-aminophenol (HO—C$_6$H$_4$—NH$_2$) | | | x |
| 5-amino-2-methylphenol (H$_2$N—C$_6$H$_3$(CH$_3$)—OH) | | | x |

TABLE F-continued
Dye Combinations
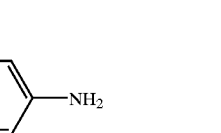
| | | | | | | | | | |
|---|---|---|---|---|---|---|---|---|---|
| | x | x | x | x | x | x | x | x | x |
TABLE G
Dye Combinations
| Structure | C102 | C103 | C104 | C105 | C106 | C107 | C108 | C109 | C110 | C111 | C112 | C113 | C114 | C115 | C116 |
|---|---|---|---|---|---|---|---|---|---|---|---|---|---|---|---|
| 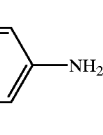 | x | x | x | x | x | x | x | x | x | x | x | x | x | x | x |
| 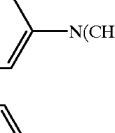 | | | | | | | | | | | | | | | |
| 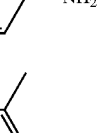 | x | x | x | x | x | x | x | | | | | | | | |
| 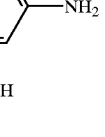 | | | | | | | | | | | | | | | |
| 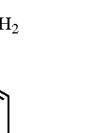 | | | | | | | | | | | | | | | |
| 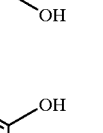 | | | | | | | | | | | | | | | |
|  | | | | | | | | | x | | | | | | |
| | | x | | | | | | | | | | x | | | |

TABLE G-continued

| Structure | C102 | C103 | C104 | C105 | C106 | C107 | C108 | C109 | C110 | C111 | C112 | C113 | C114 | C115 | C116 |
|---|---|---|---|---|---|---|---|---|---|---|---|---|---|---|---|
| naphthalen-1-ol | | | | x | | | | | | x | | | | | |
| 2-methyl-naphthalen-1-ol | | | | | x | | | | | | x | | | | |
| 2-amino-4-(2-hydroxyethoxy)aniline | | | | | | x | | | | | | x | | | |
| benzene-1,3-diamine | | | | | | | x | | | | | | x | | |
| 3-amino-phenol | | | | | | | | x | | | | | | x | |
| 5-amino-2-methyl-phenol | | | | | | | | | x | | | | | | x |
| 4,5-diamino-1-(2-hydroxyethyl)pyrazole | x | x | x | x | x | x | x | x | x | x | x | x | x | x | x |

Especially preferred combinations of hair coloring components employing a quaternized pyrrolidine primary intermediate of this invention are shown in the combinations D1 to D116 in Tables H through N. For example, in Example No. D1 of Table H, [1-(4-amino-phenyl)-pyrrolidin-yl]-trimethyl-ammonium chloride, a compound of formula (1) of this invention (Row 1 of Table H) can be combined with 2-amino-phenol (Row 7 of Table H) and in Example D3 of Table H, [1-(4-amino-phenyl)-pyrrolidin-yl]-trimethyl-ammonium chloride, a compound of formula (1) of this invention (Row 1 of Table H) can be combined with 2-methyl-benzene-1,3-diol (Row 9 of Table H).

TABLE H

| Structure | IUPAC Name | Name | D1 | D2 | D3 | D4 | D5 | D6 | D7 | D8 | D9 | D10 | D11 |
|---|---|---|---|---|---|---|---|---|---|---|---|---|---|
| [1-(4-amino-phenyl)-pyrrolidin-yl]-trimethyl-ammonium CH₃OSO₃⁻ | [1-(4-Amino-phenyl)-pyrrolidin-yl]-trimethyl-ammonium chloride | | x | x | x | x | x | x | x | x | x | x | x |

TABLE H-continued

Dye Combinations

| Structure | IUPAC Name | Name | D1 | D2 | D3 | D4 | D5 | D6 | D7 | D8 | D9 | D10 | D11 |
|---|---|---|---|---|---|---|---|---|---|---|---|---|---|
| (structure) | 2-Methyl-benzene-1,4-diamine | p-Toluene-diamine | | | | | | | | | | | |
| (structure) | Benzene-1,4-diamine | p-Phenylene-diamine | | | | | | | | | | | |
| (structure) | 2-[(4-Amino-phenyl)-(2-hydroxy-ethyl)-amino]-ethanol | N,N-Bis(2-hydroxyethyl)-p-phenylene-diamine | | | | | | | | | | | |
| (structure) | 4-Amino-phenol | p-Aminophenol | | | | | | | | | | X | X |
| (structure) | 4-Amino-3-methyl-phenol | 3-Methyl-p-aminophenol | | | | | | | | | | | |
| (structure) | 2-Amino-phenol | o-Aminophenol | X | | | | | | | | | X | |
| (structure) | Benzene-1,3-diol | Resorcinol | | X | | | | | | | | | X |
| (structure) | 2-Methyl-benzene-1,3-diol | 2-Methyl-resorcinol | | | | X | | | | | | | |
| (structure) | Naphthalen-1-ol | 1-Naphthol | | | | | X | | | | | | |
| (structure) | 2-Methyl-naphthalen-1-ol | 2-Methyl-1-naphthol | | | | | | X | | | | | |
| (structure) | 2-(2,4-Diamino-phenoxy)-ethanol | 2,4-Diamino-phenoxyethnaol | | | | | | X | | | | | |

TABLE H-continued

Dye Combinations

| Structure | IUPAC Name | Name | D1 | D2 | D3 | D4 | D5 | D6 | D7 | D8 | D9 | D10 | D11 |
|---|---|---|---|---|---|---|---|---|---|---|---|---|---|
| (H₂N–C₆H₄–NH₂, 1,3) | Benzene-1,3-diamine | m-Phenylene-diamine | | | | | | | | X | | | |
| (HO–C₆H₄–NH₂, 3-amino) | 3-Amino-phenol | m-Aminophenol | | | | | | | | | X | | |
| (H₂N–C₆H₃(CH₃)–OH) | 5-Amino-2-methyl-phenol | 2-Hydroxy-4-aminotoluene | | | | | | | | | | X | |
| (2-(4,5-Diamino-pyrazol-1-yl)-ethanol structure) | 2-(4,5-Diamino-pyrazol-1-yl)-ethanol | 1-Hydroxyethyl-4,5-diamino-pyrazole | | | | | | | | | | | |

TABLE I

Dye Combinations

| Structure | D12 | D13 | D14 | D15 | D16 | D17 | D18 | D19 | D20 |
|---|---|---|---|---|---|---|---|---|---|
| (Pyrrolidinyl aniline with quaternary ammonium, R, R', R'', X⁻) | X | X | X | X | X | X | X | X | X |
| (2-methyl-1,4-phenylenediamine) | | | | | | | | | |
| (1,4-phenylenediamine) | | | | | | | | | |
| (N,N-bis(2-hydroxyethyl)-p-phenylenediamine) | | | | | | | | | |
| (4-aminophenol) | X | X | X | X | X | X | X | | |
| (2-methyl-4-aminophenol) | | | | | | | X | X | |
| (2-aminophenol) | | | | | | | | | X |

TABLE I-continued

Dye Combinations

| Structure | | | | | | | | | X |
|---|---|---|---|---|---|---|---|---|---|
| resorcinol | | | | | | | | | |
| 2-methylresorcinol | X | | | | | | | | |
| 1-naphthol | | X | | | | | | | |
| 2-methyl-1-naphthol | | | X | | | | | | |
| 2-amino-4-(2-hydroxyethoxy)aniline | | | | X | | | | | |
| m-phenylenediamine | | | | | X | | | | |
| 3-aminophenol | | | | | | X | | | |
| 5-amino-2-methylphenol | | | | | | | X | | |
| 4,5-diamino-1-(2-hydroxyethyl)pyrazole | | | | | | | | | |

| Structure | D21 | D22 | D23 | D24 | D25 | D26 | D27 | D28 | D29 |
|---|---|---|---|---|---|---|---|---|---|
| pyrrolidine-aniline quaternary ammonium | X | X | X | X | X | X | X | X | X |

TABLE I-continued

Dye Combinations

| Structure | | | | | | | | | |
|---|---|---|---|---|---|---|---|---|---|
| 2-methyl-1,4-phenylenediamine (H$_2$N—C$_6$H$_3$(CH$_3$)—NH$_2$) | | | | | | | | | |
| 1,4-phenylenediamine (H$_2$N—C$_6$H$_4$—NH$_2$) | | | | | | | | | |
| H$_2$N—C$_6$H$_4$—N(CH$_2$CH$_2$OH)$_2$ | | | | | | | | | |
| 4-aminophenol (HO—C$_6$H$_4$—NH$_2$) | | | | | | | | | |
| 4-amino-2-methylphenol (HO—C$_6$H$_3$(CH$_3$)—NH$_2$) | X | X | X | X | X | X | X | | |
| 2-aminophenol | | | | | | | | | |
| resorcinol (1,3-dihydroxybenzene) | | | | | | | | X | X |
| 2-methylresorcinol | X | | | | | | X | | |
| 1-naphthol | X | | | | | | X | | |
| 2-methyl-1-naphthol | | | | X | | | | | |
| 2,4-diamino-1-(2-hydroxyethoxy)benzene | | | | X | | | | | |
| 1,3-phenylenediamine (H$_2$N—C$_6$H$_4$—NH$_2$) | | | | | X | | | | |

TABLE I-continued

Dye Combinations

| Structure | | | | | | | | | |
|---|---|---|---|---|---|---|---|---|---|
| 3-aminophenol (HO-C6H4-NH2) | | | | | | X | | | |
| 2-methyl-5-aminophenol (H2N-C6H3(CH3)-OH) | | | | | | | X | | |
| 4,5-diamino-1-(2-hydroxyethyl)pyrazole | | | | | | | | | |

TABLE J

Dye Combinations

| Structure | D30 | D31 | D32 | D33 | D34 | D35 | D36 | D37 | D38 |
|---|---|---|---|---|---|---|---|---|---|
| Pyrrolidine-aniline quaternary ammonium compound | X | X | X | X | X | X | X | X | X |
| 2-methyl-1,4-phenylenediamine | | | | | | X | X | X | X |
| 1,4-phenylenediamine | | | | | | | | | |
| N,N-bis(2-hydroxyethyl)-1,4-phenylenediamine | | | | | | | | | |
| 4-aminophenol | | | | | | | | | |
| 2-methyl-4-aminophenol | | | | | | | | | |
| 2-aminophenol | | | | | | X | | | |
| resorcinol | X | X | X | X | X | X | X | X | X |

TABLE J-continued
Dye Combinations
| Structure | | | | | | | | | |
|---|---|---|---|---|---|---|---|---|---|
| 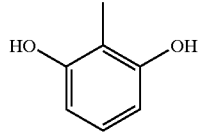 | | | | | | | X | | |
| 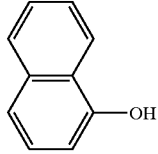 | | | | | | | | X | |
| 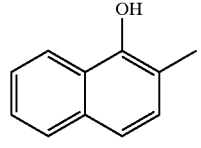 | X | | | | | | | | X |
| 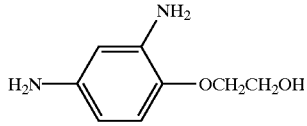 | X | | | | | | | | |
| 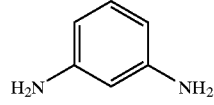 | | | X | | | | | | |
| 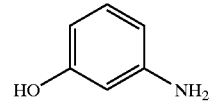 | | | | X | | | | | |
| 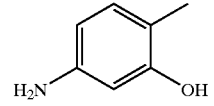 | | | | | X | | | | |
| 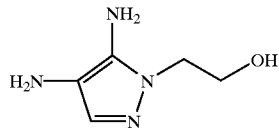 | | | | | | | | | |
| Structure | D39 | D40 | D41 | D42 | D43 | D44 | D45 | D46 | D47 |
|---|---|---|---|---|---|---|---|---|---|
| 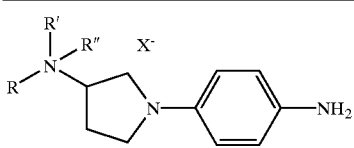 | X | X | X | X | X | X | X | X | X |
| 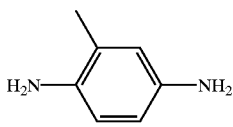 | | X | X | X | X | | | | |
|  | | | | | X | X | X | X | X |

TABLE J-continued

Dye Combinations

| Structure | | | | | | | | | | | |
|---|---|---|---|---|---|---|---|---|---|---|---|
| H₂N—C₆H₄—N(CH₂CH₂OH)₂ | | | | | | | | | | | |
| HO—C₆H₄—NH₂ | | | | | | | | | | | |
| HO—C₆H₃(CH₃)—NH₂ | | | | | | | | | | | |
| 2-aminophenol (OH, NH₂) | | | | | | X | | | | | |
| resorcinol (HO, OH) | X | X | X | X | X | X | X | X | X | | |
| 2-methylresorcinol | | | | | | | | X | | | |
| 1-naphthol | | | | | | | | X | | | |
| 2-methyl-1-naphthol | | | | | | | | | | X | |
| 2,4-diamino-1-(2-hydroxyethoxy)benzene | X | | | | | | | | | X | |
| m-phenylenediamine (H₂N, NH₂) | | | X | | | | | | | | |
| 3-aminophenol (HO, NH₂) | | | X | | | | | | | | |

TABLE J-continued
Dye Combinations
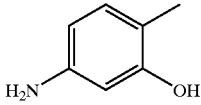   X
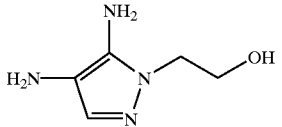
TABLE K
Dye Combinations
| Structure | D48 | D49 | D50 | D51 | D52 | D53 | D54 | D55 | D56 |
|---|---|---|---|---|---|---|---|---|---|
| 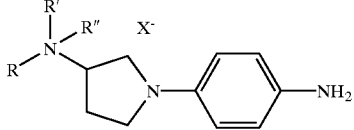 | X | X | X | X | X | X | X | X | X |
| 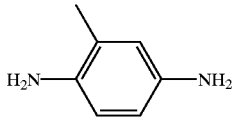 | | | | | | | | | |
|  | X | X | X | | | | | | |
| 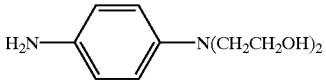 | | | | | | | | | |
|  | | | | X | X | X | X | X | X |
| 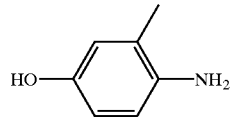 | | | | | | | | | |
| 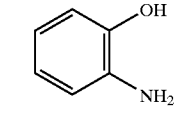 | | | | | | | | | |
| 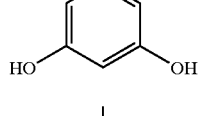 | X | X | X | X | X | X | X | X | X |
| 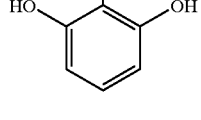 | | | | | X | | | | |

TABLE K-continued

Dye Combinations

| Structure | | | | | | | | | |
|---|---|---|---|---|---|---|---|---|---|
| 1-naphthol | | | | X | | | | | |
| 2-methyl-1-naphthol | | | | | X | | | | |
| 2,4-diamino-1-(2-hydroxyethoxy)benzene | | | | | | X | | | |
| m-phenylenediamine | | X | | | | | | X | |
| 3-aminophenol | | | X | | | | | | |
| 5-amino-2-methylphenol | | | X | | | | | | |
| 4,5-diamino-1-(2-hydroxyethyl)pyrazole | | | | | | | | | |

| Structure | D57 | D58 | D59 | D60 | D61 | D62 | D63 | D64 | D65 |
|---|---|---|---|---|---|---|---|---|---|
| pyrrolidine quaternary ammonium p-aminophenyl | X | X | X | X | X | X | X | X | X |
| 2-methyl-1,4-diaminobenzene | | | | | | | | | |
| 1,4-diaminobenzene | | | | | | | | | |
| N,N-bis(2-hydroxyethyl)-p-phenylenediamine | | | | | | | | | |

TABLE K-continued

| Dye Combinations | | | | | | | | | |
|---|---|---|---|---|---|---|---|---|---|
| 4-aminophenol (HO—C6H4—NH2) | X | X | | | | | | | |
| 2-methyl-4-aminophenol | | | X | X | X | X | X | X | X |
| 2-aminophenol | | | X | | | | | | |
| 1,3-dihydroxybenzene (resorcinol) | X | X | X | X | X | X | X | X | X |
| 2-methyl-1,3-dihydroxybenzene | | | | X | | | | | |
| 1-naphthol | | | | X | | | | | |
| 2-methyl-1-naphthol | | | | | | X | | | |
| 2,4-diamino-1-(2-hydroxyethoxy)benzene | | | | | | | X | | |
| 1,3-diaminobenzene | | | | | | | | X | |
| 3-aminophenol | | X | | | | | | | X |
| 5-amino-2-methylphenol | | X | | | | | | | |

TABLE K-continued

Dye Combinations

[Structure: 4,5-diamino-1-(2-hydroxyethyl)pyrazole]

TABLE L

Dye Combinations

| Structure | D66 | D67 | D68 | D69 | D70 | D71 | D72 | D73 | D74 |
|---|---|---|---|---|---|---|---|---|---|
| [pyrrolidine-aniline quaternary ammonium] | X | X | X | X | X | X | X | X | X |
| [2-methyl-1,4-phenylenediamine] | | | | | | | | | |
| [1,4-phenylenediamine] | | | | | | | | | |
| [H₂N–C₆H₄–N(CH₂CH₂OH)₂] | | X | X | X | X | X | X | X | X |
| [4-aminophenol] | | | | | | | | | |
| [2-methyl-4-aminophenol] | X | | | | | | | | |
| [2-aminophenol] | | | | | | | | | |
| [resorcinol] | X | X | | | | | | | |
| [2-methylresorcinol] | | | | X | | | | | |

TABLE L-continued

Dye Combinations

| Structure | | | | | | | | | |
|---|---|---|---|---|---|---|---|---|---|
| 1-naphthol | X | | | | | | | | |
| 2-methyl-1-naphthol | | X | | | | | | | |
| 2,4-diamino-1-(2-hydroxyethoxy)benzene | | | X | | | | | | |
| m-phenylenediamine | | | | X | | | | | |
| 3-aminophenol | | | | | | X | | | |
| 2-methyl-5-aminophenol | X | | | | | | | X | |
| 4,5-diamino-1-(2-hydroxyethyl)pyrazole | | | | | | | | | |

| Structure | D75 | D76 | D77 | D78 | D79 | D80 | D81 | D82 | D83 |
|---|---|---|---|---|---|---|---|---|---|
| pyrrolidine-aminophenyl quaternary ammonium (R, R', R'', X⁻) | X | X | X | X | X | X | X | X | X |
| 2-methyl-p-phenylenediamine | | | | | | | | | |
| p-phenylenediamine | | | | | | | | | |
| N,N-bis(2-hydroxyethyl)-p-phenylenediamine | | | | | | | | | |

TABLE L-continued

Dye Combinations

| Structure | 1 | 2 | 3 | 4 | 5 | 6 | 7 | 8 | 9 |
|---|---|---|---|---|---|---|---|---|---|
| HO—C₆H₄—NH₂ (4-aminophenol) | X | X | X | X | X | X | X | X | X |
| HO—C₆H₃(CH₃)—NH₂ (2-methyl-4-aminophenol) | | | | | | | | | |
| 2-aminophenol | X | | | | | | | | |
| Resorcinol (1,3-dihydroxybenzene) | | X | | | | | | | |
| 2-methylresorcinol | | | X | | | | | | |
| 1-naphthol | | | | X | | | | | |
| 2-methyl-1-naphthol | | | | | X | | | | |
| 2,4-diamino-1-(2-hydroxyethoxy)benzene | | | | | | X | | | |
| m-phenylenediamine | | | | | | | X | | |
| 3-aminophenol | | | | | | | | X | |
| 5-amino-2-methylphenol | | | | | | | | | X |

TABLE L-continued

Dye Combinations

| Structure | |
|---|---|
| (5-amino-4-amino-1-(2-hydroxyethyl)pyrazole) | x |

TABLE M

Dye Combinations

| Structure | D84 | D85 | D86 | D87 | D88 | D89 | D90 | D91 | D92 |
|---|---|---|---|---|---|---|---|---|---|
| (pyrrolidine-aniline quaternary ammonium) | X | X | X | X | X | X | X | X | X |
| 2-methyl-1,4-phenylenediamine | | | | | | | | | |
| 1,4-phenylenediamine | | | | | | | | | |
| N,N-bis(2-hydroxyethyl)-p-phenylenediamine | | | | | | | | | |
| 4-aminophenol | | | | | | | | | |
| 4-amino-3-methylphenol | X | X | X | X | X | X | X | X | X |
| 2-amino-phenol | X | | | | | | | | |
| resorcinol | | X | | | | | | | |
| 2-methylresorcinol | | | X | | | | | | |

TABLE M-continued

Dye Combinations

| Structure | | | | | | | | | |
|---|---|---|---|---|---|---|---|---|---|
| 1-naphthol (OH on naphthalene) | | | X | | | | | | |
| 2-methyl-1-naphthol | | | | X | | | | | |
| 2,4-diamino-phenoxyethanol | | | | | X | | | | |
| m-phenylenediamine | | | | | | X | | | |
| 3-aminophenol | | | | | | | X | | |
| 5-amino-2-methylphenol | | | | | | | | X | |
| 4,5-diamino-1-(2-hydroxyethyl)pyrazole | X | X | X | X | X | X | X | X | x |

| Structure | D93 | D94 | D95 | D96 | D97 | D98 | D99 | D100 | D101 |
|---|---|---|---|---|---|---|---|---|---|
| pyrrolidinyl aniline with quaternary ammonium (R, R', R'', N+ X−) | X | X | X | X | X | X | X | X | X |
| 2-methyl-p-phenylenediamine | X | X | X | X | X | X | X | X | |
| p-phenylenediamine | | | | | | | | | X |
| N,N-bis(2-hydroxyethyl)-p-phenylenediamine | | | | | | | | | |

TABLE M-continued

Dye Combinations

| Structure | | | |
|---|---|---|---|
| HO—⟨⟩—NH₂ | | | |
| HO—⟨CH₃⟩—NH₂ | | | |
| ⟨⟩(OH)(NH₂) | | | |
| HO—⟨⟩—OH (resorcinol) | X | | X |
| HO—⟨CH₃⟩—OH | | X | |
| naphthalen-1-ol | | X | |
| 2-methylnaphthalen-1-ol | | X | |
| H₂N—⟨NH₂⟩—OCH₂CH₂OH | | X | |
| H₂N—⟨⟩—NH₂ (m-phenylenediamine) | | | X |
| HO—⟨⟩—NH₂ (3-aminophenol) | | | X |
| H₂N—⟨CH₃⟩—OH | | | X |

TABLE M-continued

Dye Combinations

| Structure | | | | | | | | | |
|---|---|---|---|---|---|---|---|---|---|
| 4,5-diamino-1-(2-hydroxyethyl)pyrazole | X | X | X | X | X | X | X | X | x |

TABLE N

Dye Combinations

| Structure | D102 | D103 | D104 | D105 | D106 | D107 | D108 | D109 | D110 | D111 | D112 | D113 | D114 | D115 | D116 |
|---|---|---|---|---|---|---|---|---|---|---|---|---|---|---|---|
| N,N,N-trialkyl-pyrrolidinium-aniline | X | X | X | X | X | X | X | X | X | X | X | X | X | X | X |
| 2-methyl-1,4-phenylenediamine | | | | | | | | | | | | | | | |
| 1,4-phenylenediamine | X | X | X | X | X | X | X | | | | | | | | |
| N,N-bis(2-hydroxyethyl)-p-phenylenediamine | | | | | | | | | | | | | | | |
| 4-aminophenol | | | | | | | | | | | | | | | |
| 2-methyl-4-aminophenol | | | | | | | | | | | | | | | |
| 2-aminophenol | | | | | | | | | | | | | | | |
| resorcinol | | | | | | | | | | | X | | | | |
| 2-methylresorcinol | | | | | | | | | | | | | | | |

TABLE N-continued

| | Dye Combinations | | | | | | | | | | | | | | |
|---|---|---|---|---|---|---|---|---|---|---|---|---|---|---|---|
| Structure | D102 | D103 | D104 | D105 | D106 | D107 | D108 | D109 | D110 | D111 | D112 | D113 | D114 | D115 | D116 |
| 2-methyl-benzene-1,3-diol | X | | | | | | | | X | | | | | | |
| 1-naphthol | | X | | | | | | | | X | | | | | |
| 2-methyl-1-naphthol | | | X | | | | | | | | X | | | | |
| 2-amino-4-(2-hydroxyethoxy)-aniline | | | | X | | | | | | | | X | | | |
| m-phenylenediamine | | | | | X | | | | | | | | X | | |
| 3-amino-phenol | | | | | | X | | | | | | | | X | |
| 5-amino-2-methyl-phenol | | | | | | | X | | | | | | | | X |
| 4,5-diamino-1-(2-hydroxyethyl)-pyrazole | X | X | X | X | X | X | X | X | X | X | X | X | X | X | x |

Other especially preferred combinations of hair coloring components employing a quaternized pyrrolidine primary intermediate of this invention are shown in the combinations D1 to D116 in Tables O through U. For example, in Example No. D1 of Table O, [1-(4-amino-phenyl)-pyrrolidin-yl]-trimethyl-ammonium sulfate, a compound of formula (1) of this invention (Row 1 of Table O) can be combined with 2-amino-phenol (Row 7 of Table O) and in Example D3 of Table O, [1-(4-amino-phenyl)-pyrrolidin-yl]-trimethyl-ammonium sulfate, a compound of formula (1) of this invention (Row 1 of Table O) can be combined with 2-methyl-benzene-1,3-diol (Row 9 of Table O).

TABLE O

Dye Combinations

| Structure | IUPAC Name | Name | D1 | D2 | D3 | D4 | D5 | D6 | D7 | D8 | D9 | D10 | D11 |
|---|---|---|---|---|---|---|---|---|---|---|---|---|---|
| (structure with CH₃OSO₃⁻, N⁺(CH₃)₃, pyrrolidine, phenyl-NH₂) | [1-(4-Amino-phenyl)-pyrrolidin-yl]-trimethyl-ammonium chloride | | X | X | X | X | X | X | X | X | X | X | X |
| (2-methyl-1,4-diaminobenzene) | 2-Methyl-benzene-1,4-diamine | p-Toluene-diamine | | | | | | | | | | | |
| (1,4-diaminobenzene) | Benzene-1,4-diamine | p-Phenylene-diamine | | | | | | | | | | | |
| (H₂N-C₆H₄-N(CH₂CH₂OH)₂) | 2-[(4-Amino-phenyl)-(2-hydroxy-ethyl)-amino]-ethanol | N,N-Bis(2-hydroxyethyl)-p-phenylene-diamine | | | | | | | | | | | |
| (HO-C₆H₄-NH₂) | 4-Amino-phenol | p-Aminophenol | | | | | | | | | | X | X |
| (4-amino-3-methylphenol) | 4-Amino-3-methyl-phenol | 3-Methyl-p-aminophenol | | | | | | | | | | | |
| (2-aminophenol) | 2-Amino-phenol | o-Aminophenol | X | | | | | | | | | X | |
| (1,3-dihydroxybenzene) | Benzene-1,3-diol | Resorcinol | | | X | | | | | | | | X |
| (2-methylresorcinol) | 2-Methyl-benzene-1,3-diol | 2-Methyl-resorcinol | | | | | X | | | | | | |
| (1-naphthol) | Naphthalen-1-ol | 1-Naphthol | | | | | | | X | | | | |
| (2-methyl-1-naphthol) | 2-Methyl-naphthalen-1-ol | 2-Methyl-1-naphthol | | | | | | | | X | | | |

TABLE O-continued

Dye Combinations

| Structure | IUPAC Name | Name | D1 | D2 | D3 | D4 | D5 | D6 | D7 | D8 | D9 | D10 | D11 |
|---|---|---|---|---|---|---|---|---|---|---|---|---|---|
| H₂N-⌬(NH₂)-OCH₂CH₂OH | 2-(2,4-Diamino-phenoxy)-ethanol | 2,4-Diamino-phenoxyethnaol | | | | | | X | | | | | |
| H₂N-⌬-NH₂ | Benzene-1,3-diamine | m-Phenylene-diamine | | | | | | | | X | | | |
| HO-⌬-NH₂ | 3-Amino-phenol | m-Aminophenol | | | | | | | | | X | | |
| H₂N-⌬(CH₃)-OH | 5-Amino-2-methyl-phenol | 2-Hydroxy-4-aminotoluene | | | | | | | | | | X | |
| H₂N-(pyrazole)-OH | 2-(4,5-Diamino-pyrazol-1-yl)-ethanol | 1-Hydroxyethyl-4,5-diamino-pyrazole | | | | | | | | | | | |

TABLE P

Dye Combinations

| Structure | D12 | D13 | D14 | D15 | D16 | D17 | D18 | D19 | D20 |
|---|---|---|---|---|---|---|---|---|---|
| (CH₃)₃N⁺-pyrrolidine-⌬-NH₂ · CH₃OSO₃⁻ | X | X | X | X | X | X | X | X | X |
| H₂N-⌬(CH₃)-NH₂ | | | | | | | | | |
| H₂N-⌬-NH₂ | | | | | | | | | |
| H₂N-⌬-N(CH₂CH₂OH)₂ | | | | | | | | | |
| HO-⌬-NH₂ | X | X | X | X | X | X | X | | |

TABLE P-continued
| Dye Combinations | | | | | |
|---|---|---|---|---|---|
| 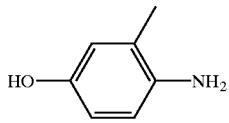 |  |  |  | X | X |
| 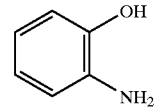 |  |  |  | X |  |
| 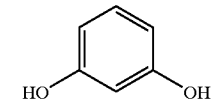 |  |  |  | X |  |
| 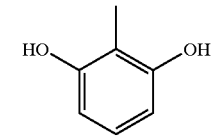 | X |  |  |  |  |
| 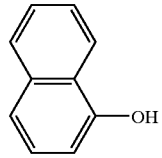 |  | X |  |  |  |
| 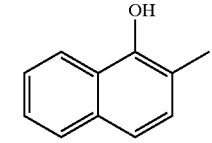 |  | X |  |  |  |
| 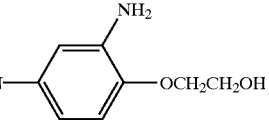 |  | X |  |  |  |
| 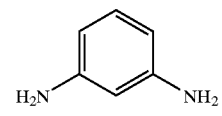 |  |  | X |  |  |
| 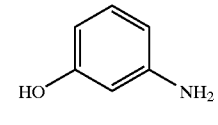 |  |  | X |  |  |
| 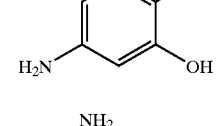 |  |  |  | X |  |
| 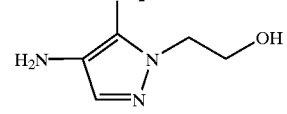 |  |  |  |  |  |

TABLE P-continued
Dye Combinations
| Structure | D21 | D22 | D23 | D24 | D25 | D26 | D28 | D29 | |
|---|---|---|---|---|---|---|---|---|---|
| 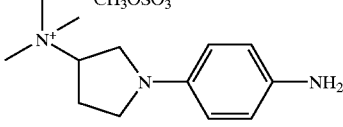 | X | X | X | X | X | X | X | X | X |
| 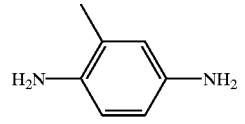 | | | | | | | | | |
|  | | | | | | | | | |
| 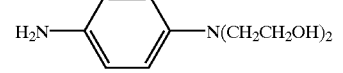 | | | | | | | | | |
| 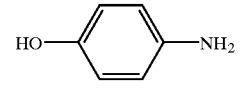 | | | | | | | | | |
| 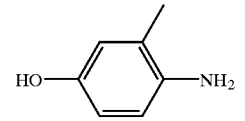 | X | X | X | X | X | X | X | | |
| 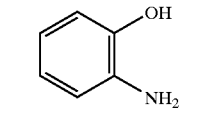 | | | | | | | | | |
| 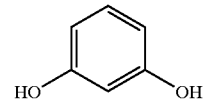 | | | | | | | | X | X |
| 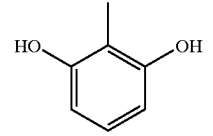 | X | | | | | X | | | |
| 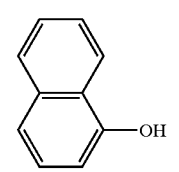 | | | X | | | | | X | |
| 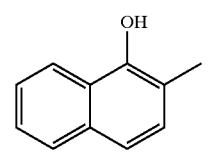 | | | X | | | | | | |

TABLE P-continued

| Dye Combinations | |
|---|---|
| ![structure: 2,4-diamino-phenoxyethanol] H₂N-C₆H₃(NH₂)-OCH₂CH₂OH | X |
| ![structure: m-phenylenediamine] H₂N-C₆H₄-NH₂ | X |
| ![structure: 3-aminophenol] HO-C₆H₄-NH₂ | X |
| ![structure: 5-amino-2-methylphenol] H₂N-C₆H₃(CH₃)-OH | X |
| ![structure: 4,5-diamino-1-(2-hydroxyethyl)pyrazole] H₂N-pyrazole-N-CH₂CH₂OH, NH₂ | |

TABLE Q

| Structure | D30 | D31 | D32 | D33 | D34 | D35 | D36 | D37 | D38 |
|---|---|---|---|---|---|---|---|---|---|
| (CH₃)₃N⁺-pyrrolidine-N-C₆H₄-NH₂ · CH₃OSO₃⁻ | X | X | X | X | X | X | X | X | X |
| H₂N-C₆H₃(CH₃)-NH₂ (2-methyl-p-phenylenediamine) | | | | | | X | X | X | X |
| H₂N-C₆H₄-NH₂ | | | | | | | | | |
| H₂N-C₆H₄-N(CH₂CH₂OH)₂ | | | | | | | | | |
| HO-C₆H₄-NH₂ | | | | | | | | | |
| HO-C₆H₃(CH₃)-NH₂ | | | | | | | | | |

TABLE Q-continued

Dye Combinations

| Structure | D39 | D40 | D41 | D42 | D43 | D44 | D45 | D46 | D47 |
|---|---|---|---|---|---|---|---|---|---|
| 2-aminophenol | | | | | | X | | | |
| resorcinol | X | X | X | X | X | X | X | X | X |
| 2-methylresorcinol | | | | | | | X | | |
| 1-naphthol | | | | | | | | X | |
| 2-methyl-1-naphthol | X | | | | | | | | X |
| 2,4-diamino-1-(β-hydroxyethyloxy)benzene | X | | | | | | | | |
| m-phenylenediamine | | | X | | | | | | |
| 3-aminophenol | | | | | X | | | | |
| 5-amino-2-methylphenol | | | | | | X | | | |
| 4,5-diamino-1-(β-hydroxyethyl)pyrazole | | | | | | | | | |

| Structure | D39 | D40 | D41 | D42 | D43 | D44 | D45 | D46 | D47 |
|---|---|---|---|---|---|---|---|---|---|
| trimethylammonium pyrrolidinyl-aminophenyl, CH₃OSO₃⁻ | X | X | X | X | X | X | X | X | X |

TABLE Q-continued

Dye Combinations

| Structure | | | | | | | | | | |
|---|---|---|---|---|---|---|---|---|---|---|
| 2-methyl-1,4-phenylenediamine | x | x | x | x | | | | | | |
| 1,4-phenylenediamine | | | | | x | x | x | x | x | |
| 4-amino-N,N-bis(2-hydroxyethyl)aniline | | | | | | | | | | |
| 4-aminophenol | | | | | | | | | | |
| 2-methyl-4-aminophenol | | | | | | | | | | |
| 2-aminophenol | | | | x | | | | | | |
| resorcinol | x | x | x | x | x | x | x | x | x | |
| 2-methylresorcinol | | | | | x | | | | | |
| 1-naphthol | | | | | x | | | | | |
| 2-methyl-1-naphthol | | | | | | | x | | | |
| 2-amino-4-(2-hydroxyethoxy)aniline | x | | | | | | | | x | |

TABLE Q-continued

| Dye Combinations | |
|---|---|
| 1,3-diaminobenzene (H₂N-C₆H₄-NH₂) | X |
| 3-aminophenol (HO-C₆H₄-NH₂) | X |
| 5-amino-2-methylphenol (H₂N-C₆H₃(CH₃)-OH) | X |
| 4,5-diamino-1-(2-hydroxyethyl)pyrazole | |

TABLE R

| Structure | D48 | D49 | D50 | D51 | D52 | D53 | D54 | D55 | D56 |
|---|---|---|---|---|---|---|---|---|---|
| trimethyl-[1-(4-aminophenyl)pyrrolidin-3-yl]ammonium methylsulfate | X | X | X | X | X | X | X | X | X |
| 2-methyl-1,4-diaminobenzene | | | | | | | | | |
| 1,4-diaminobenzene | X | X | X | | | | | | |
| N,N-bis(2-hydroxyethyl)-p-phenylenediamine | | | | | | | | | |
| 4-aminophenol | | | | X | X | X | X | X | X |
| 2-methyl-4-aminophenol | | | | | | | | | |
| 2-aminophenol | | | | | | | | | |

TABLE R-continued

Dye Combinations

| Structure | | | | | | | | | |
|---|---|---|---|---|---|---|---|---|---|
| resorcinol | X | X | X | X | X | X | X | X | X |
| 2-methylresorcinol | | | | | X | | | | |
| 1-naphthol | | | | | X | | | | |
| 2-methyl-1-naphthol | | | | | | | X | | |
| 2,4-diamino-1-(β-hydroxyethyloxy)benzene | | | | | | | | X | |
| m-phenylenediamine | X | | | | | | | | X |
| m-aminophenol | | X | | | | | | | |
| 2-methyl-5-aminophenol | | | X | | | | | | |
| 4,5-diamino-1-(β-hydroxyethyl)pyrazole | | | | | | | | | |

| Structure | D57 | D58 | D59 | D60 | D61 | D62 | D63 | D64 | D65 |
|---|---|---|---|---|---|---|---|---|---|
| (trimethylammonium pyrrolidinyl-aminophenyl CH₃OSO₃⁻) | X | X | X | X | X | X | X | X | X |

TABLE R-continued

Dye Combinations

| Structure | | | | | | | | | | |
|---|---|---|---|---|---|---|---|---|---|---|
| 2-methyl-1,4-phenylenediamine | | | | | | | | | | |
| 1,4-phenylenediamine | | | | | | | | | | |
| N,N-bis(2-hydroxyethyl)-1,4-phenylenediamine | | | | | | | | | | |
| 4-aminophenol | X | X | | | | | | | | |
| 4-amino-3-methylphenol | | | X | X | X | X | X | X | X | |
| 2-aminophenol | | | X | | | | | | | |
| resorcinol | X | X | X | X | X | X | X | X | X | |
| 2-methylresorcinol | | | X | | | | | | | |
| 1-naphthol | | | | X | | | | | | |
| 2-methyl-1-naphthol | | | | | | X | | | | |
| 2-amino-4-(2-hydroxyethoxy)aniline | | | | | | | X | | | |
| 1,3-phenylenediamine | | | | | | | | X | | |

TABLE R-continued

Dye Combinations

| Structure | | | |
|---|---|---|---|
| 3-aminophenol (HO-C6H4-NH2) | X | | X |
| 2-methyl-5-aminophenol | X | | |
| 4,5-diamino-1-(2-hydroxyethyl)pyrazole | | | |

TABLE S

Dye Combinations

| Structure | D66 | D67 | D68 | D69 | D70 | D71 | D72 | D73 | D74 |
|---|---|---|---|---|---|---|---|---|---|
| Trimethylammonium pyrrolidinyl-phenyl-NH2, CH3OSO3− | X | X | X | X | X | X | X | X | X |
| 2-methyl-1,4-phenylenediamine | | | | | | | | | |
| 1,4-phenylenediamine | | | | | | | | | |
| H2N-C6H4-N(CH2CH2OH)2 | | X | X | X | X | X | X | X | X |
| 4-aminophenol | | | | | | | | | |
| 2-methyl-4-aminophenol | X | | | | | | | | |
| 2-aminophenol | | | | | | | | | |
| resorcinol | X | X | | | | | | | |

TABLE S-continued

| Dye Combinations | | | | | | | | | |
|---|---|---|---|---|---|---|---|---|---|
| 2-methylresorcinol (HO-C6H3(CH3)-OH) | | | X | | | | | | |
| 1-naphthol | | | | X | | | | | |
| 2-methyl-1-naphthol | | | | | X | | | | |
| 2-amino-4-(2-hydroxyethoxy)aniline | | | | | | X | | | |
| m-phenylenediamine | | | | | | | X | | |
| 3-aminophenol | | | | | | | | X | |
| 5-amino-2-methylphenol | | X | | | | | | | X |
| 4,5-diamino-1-(2-hydroxyethyl)pyrazole | | | | | | | | | |

| Structure | D75 | D76 | D77 | D78 | D79 | D80 | D81 | D82 | D83 |
|---|---|---|---|---|---|---|---|---|---|
| trimethyl-[1-(4-aminophenyl)pyrrolidin-3-yl]ammonium methylsulfate | X | X | X | X | X | X | X | X | X |
| 2-methyl-p-phenylenediamine | | | | | | | | | |
| p-phenylenediamine | | | | | | | | | |

TABLE S-continued

Dye Combinations

| Structure | | | | | | | | | | |
|---|---|---|---|---|---|---|---|---|---|---|
| H₂N–C₆H₄–N(CH₂CH₂OH)₂ | | | | | | | | | | |
| HO–C₆H₄–NH₂ (4-aminophenol) | X | X | X | X | X | X | X | X | X | |
| HO–C₆H₃(CH₃)–NH₂ | | | | | | | | | | |
| 2-aminophenol (OH, NH₂ ortho) | X | | | | | | | | | |
| resorcinol (1,3-dihydroxybenzene) | | X | | | | | | | | |
| 2-methylresorcinol | | | X | | | | | | | |
| 1-naphthol | | | | X | | | | | | |
| 2-methyl-1-naphthol | | | | | X | | | | | |
| 2,4-diamino-1-(2-hydroxyethoxy)benzene | | | | | | X | | | | |
| m-phenylenediamine | | | | | | | X | | | |
| 3-aminophenol | | | | | | | | X | | |

TABLE S-continued

Dye Combinations

| Structure | | | | | | | | | |
|---|---|---|---|---|---|---|---|---|---|
|  (H₂N—C₆H₃(CH₃)—OH) | | | | | | | | | X |
| 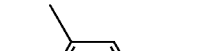 (4,5-diamino-1-(2-hydroxyethyl)pyrazole) | X | X | X | X | X | X | X | X | x |

TABLE T

Dye Combinations

| Structure | D84 | D85 | D86 | D87 | D88 | D89 | D90 | D91 | D92 |
|---|---|---|---|---|---|---|---|---|---|
| 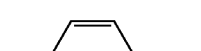 (trimethylammonium pyrrolidine aniline, CH₃OSO₃⁻) | X | X | X | X | X | X | X | X | X |
| 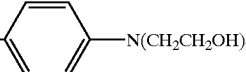 (2-methyl-1,4-phenylenediamine) | | | | | | | | | |
|  (p-phenylenediamine) | | | | | | | | | |
| 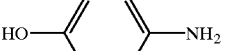 (H₂N—C₆H₄—N(CH₂CH₂OH)₂) | | | | | | | | | |
| 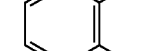 (4-aminophenol) | | | | | | | | | |
|  (2-methyl-4-amino-phenol) | X | X | X | X | X | X | X | X | X |
| 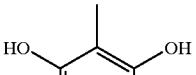 (2-aminophenol) | X | | | | | | | | |
| (resorcinol) | | X | | | | | | | |
| (2-methylresorcinol) | | | X | | | | | | |

TABLE T-continued
Dye Combinations
| Structure | | | | | | | | | |
|---|---|---|---|---|---|---|---|---|---|
| 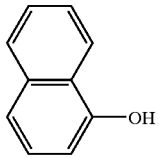 1-naphthol | | | | X | | | | | |
| 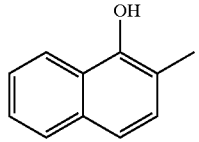 2-methyl-1-naphthol | | | X | | | | | | |
| 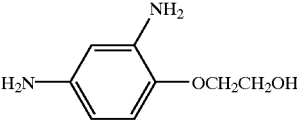 2,4-diamino-1-(β-hydroxyethyloxy)benzene | | | | | X | | | | |
| 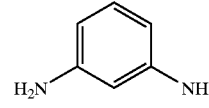 m-phenylenediamine | | | | | | X | | | |
| 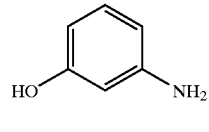 3-aminophenol | | | | | | | X | | |
| 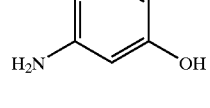 5-amino-2-methylphenol | | | | | | | | | X |
| 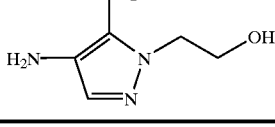 4,5-diamino-1-(β-hydroxyethyl)pyrazole | X | X | X | X | X | X | X | X | x |
| Structure | D93 | D94 | D95 | D96 | D97 | D98 | D99 | D100 | D101 |
|---|---|---|---|---|---|---|---|---|---|
| 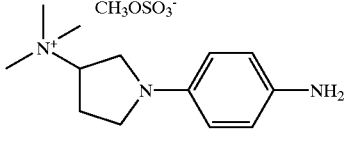 | X | X | X | X | X | X | X | X | X |
| 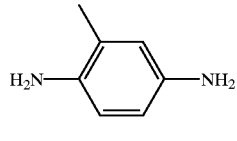 | X | X | X | X | X | X | X | X | |
| 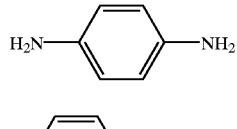 | | | | | | | | | X |
| 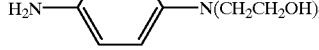 | | | | | | | | | |

TABLE T-continued

Dye Combinations

| Structure | | |
|---|---|---|
| HO—⌬—NH₂ | | |
| HO—⌬(CH₃)—NH₂ | | |
| ⌬(OH)(NH₂) | | |
| HO—⌬—OH (resorcinol) | X | X |
| HO—⌬(CH₃)—OH | X | |
| naphthalen-1-ol | X | |
| 2-methylnaphthalen-1-ol | X | |
| H₂N—⌬(NH₂)—OCH₂CH₂OH | X | |
| H₂N—⌬—NH₂ (m-phenylenediamine) | X | |
| HO—⌬—NH₂ (m-aminophenol) | X | |
| H₂N—⌬(CH₃)—OH | X | |

TABLE T-continued
| Dye Combinations |  |
|---|---|
| 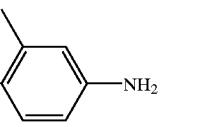 | X X X X X X X X x |
TABLE U
| Structure | Dye Combinations |||||||||||||||
|---|---|---|---|---|---|---|---|---|---|---|---|---|---|---|---|
|  | D102 | D103 | D104 | D105 | D106 | D107 | D108 | D109 | D110 | D111 | D112 | D113 | D114 | D115 | D116 |
| 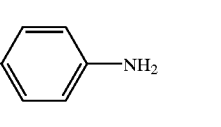 | X | X | X | X | X | X | X | X | X | X | X | X | X | X | X |
| 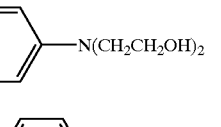 |  |  |  |  |  |  |  |  |  |  |  |  |  |  |  |
| 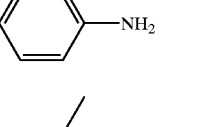 | X | X | X | X | X | X | X |  |  |  |  |  |  |  |  |
| 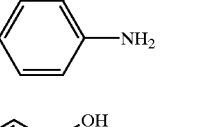 |  |  |  |  |  |  |  |  |  |  |  |  |  |  |  |
| 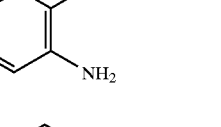 |  |  |  |  |  |  |  |  |  |  |  |  |  |  |  |
| 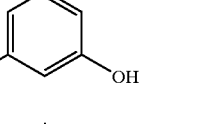 |  |  |  |  |  |  |  |  |  |  |  |  |  |  |  |
|  |  |  |  |  |  |  |  |  | X |  |  |  |  |  |  |
| 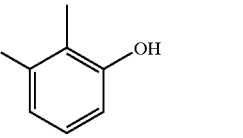 |  | X |  |  |  |  |  |  |  |  |  | X |  |  |  |

TABLE U-continued

Dye Combinations

| Structure | D102 | D103 | D104 | D105 | D106 | D107 | D108 | D109 | D110 | D111 | D112 | D113 | D114 | D115 | D116 |
|---|---|---|---|---|---|---|---|---|---|---|---|---|---|---|---|
| 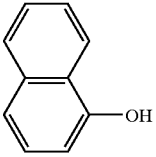 |  | X |  |  |  |  |  |  |  | X |  |  |  |  |  |
| 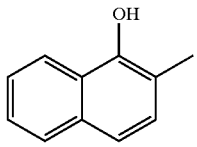 |  |  | X |  |  |  |  |  |  |  | X |  |  |  |  |
| 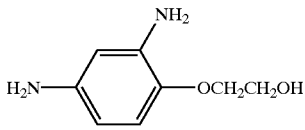 |  |  |  | X |  |  |  |  |  |  |  | X |  |  |  |
| 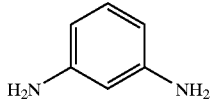 |  |  |  |  | X |  |  |  |  |  |  |  | X |  |  |
| 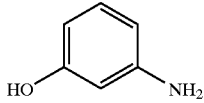 |  |  |  |  |  | X |  |  |  |  |  |  |  | X |  |
| 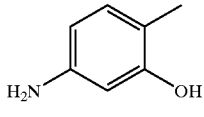 |  |  |  |  |  |  | X |  |  |  |  |  |  |  | X |
| 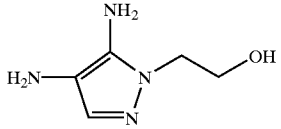 | X | X | X | X | X | X | X | X | X | X | X | X | X | X | x |

With the foregoing description of the invention, those skilled in the art will appreciate that modifications may be made to the invention without departing from the spirit thereof. Therefore, it is not intended that the scope of the invention be limited to the specific embodiments illustrated and described.

We claim:

1. In a hair coloring system comprising a composition containing one or more oxidative hair coloring agents and a composition containing one or more oxidizing agents, the improvement comprising the presence of a quaternized pyrrolidine compound of Formula (1):

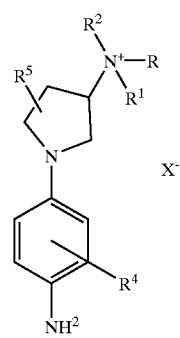 (1)

wherein X is selected from the group consisting of Cl, Br, I, or $R^3SO_4$; R is selected from the group consisting of a $C_1$ to $C_{22}$ alkyl group or a $C_1$ to $C_{22}$ mono or dihydroxyalkyl group; $R^1$ and $R^2$ are each independently a $C_1$ to $C_4$ alkyl group; $R^3$ is a $C_1$ to $C_{22}$ alkyl group or a $C_1$ to $C_{22}$ mono or dihydroxyalkyl group; $R^4$ is selected from the group consisting of a hydrogen atom, a $C_1$ to $C_5$ alkyl group or such an alkyl group substituted with one or more hydroxy or amino moieties; and $R^5$ is selected from the group consisting of a hydrogen atom or a hydroxy group as a primary intermediate in the composition containing the one or more oxidative hair coloring agents.

2. A hair coloring system according to claim 1 wherein the composition comprising one or more oxidative hair coloring agents additionally comprises one or more primary intermediate selected from the group consisting of: 2-methyl-benzene-1,4-diamine, benzene-1,4-diamine, 2-(2,5-diamino-phenyl)-ethanol, 1-(2,5-diamino-phenyl)-ethanol, 2-[(4-amino-phenyl)-(2-hydroxy-ethyl)-amino]-ethanol, 4-amino-phenol, 4-methylamino-phenol, 4-amino-3-methyl-phenol, 1-(5-amino-2-hydroxy-phenyl)-ethane-1,2-diol, 2-amino-phenol, 2-amino-5-methyl-phenol, 2-amino-6-methyl-phenol, N-(4-amino-3-hydroxy-phenyl)-acetamide, pyrimidine-2,4,5,6-tetramine and 2-(4,5-diamino-1H-pyrazol-1-yl)ethanol.

3. A hair coloring system according to claim 1 wherein the composition comprising one or more oxidative hair coloring agents additionally comprises one or more couplers selected from the group consisting of: benzene-1,3-diol, 4-chlorobenzene-1,3-diol, naphthalene-1-ol, 2-methyl-naphthalene-1 -ol, 2-methyl-benzene-1,3-diol, 2-(2,4-diamino-phenoxy)-ethanol, 2-(3-amino-4-methoxy-phenylamino)-ethanol, 2-[2,4-diamino-5-(2-hydroxy-ethoxy)-phenoxy]-ethanol, 3-(2,4-diamino-phenoxy)-propan-1-ol, 3-amino-phenol, 5-amino-2-methyl-phenol, 5-(2-hydroxy-ethylamino)-2-methyl-phenol, 3-amino-2-methyl-phenol, 3,4-dihydro-2H-1,4-benzoxazin-6-ol, 4-methyl-2-phenyl-2,4-dihydro-3H-pyrazol-3-one, and 1H-indol-6-ol, and 2-aminopyridin-3-ol.

4. A hair coloring system according to claim 1 wherein $R^1$ and $R^2$ are each $CH_3$; $R^4$ and $R^5$ are each hydrogen atoms; and X is selected from the group consisting of Cl, Br and $R^3SO_4$ where $R^3$ is $CH_3$ or $C_3H_7$.

5. A hair coloring system according to claim 1 wherein R, $R^1$ and $R^2$ are each $CH_3$; $R^4$ and $R^5$ are each hydrogen; and X is Cl or $R^3SO_4$ where $R^3$ is $CH_3$.

6. In a system for coloring hair wherein at least one primary intermediate is reacted with at least one coupler in the presence of an oxidizing agent to produce an oxidative hair dye, the improvement wherein a quaternized pyrrolidine compound of Formula (1):

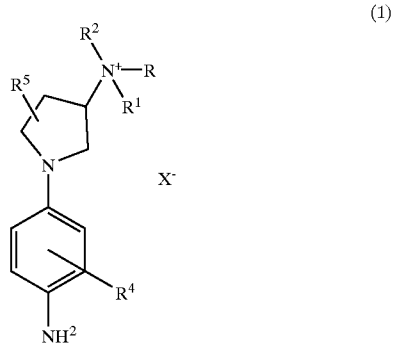

(1)

wherein X is selected from the group consisting of Cl, Br, I, or $R^3SO_4$; R is selected from the group consisting of a $C_1$ to $C_{22}$ alkyl group or a $C_1$ to $C_{22}$ mono or dihydroxyalkyl group; $R^1$ and $R^2$ are each independently a $C_1$ to $C_4$ alkyl group; $R^3$ is a $C_1$ to $C_{22}$ alkyl group or a $C_1$ to $C_{22}$ mono or dihydroxyalkyl group; $R^4$ is selected from the group consisting of a hydrogen atom, a $C_1$ to $C_5$ alkyl group or such an alkyl group substituted with one or more hydroxy or amino moieties; and $R^5$ is selected from the group consisting of a hydrogen atom or a hydroxy group is employed as a primary intermediate.

7. A system for coloring hair according to claim 6 wherein the system additionally comprises one or more primary intermediates selected from the group consisting of: 2-methyl-benzene-1,4-diamine, benzene-1,4-diamine, 2-(2,5-diamino-phenyl)-ethanol, 1-(2,5-diamino-phenyl)-ethanol, 2-[(4-amino-phenyl)-(2-hydroxy-ethyl)-amino]-ethanol, 4-amino-phenol, 4-methylamino-phenol, 4-amino-3-methyl-phenol, 1-(5-amino-2-hydroxy-phenyl)-ethane-1,2-diol, 2-amino-phenol, 2-amino-5-methyl-phenol, 2-amino-6-methyl-phenol, N-(4-amino-3-hydroxy-phenyl)-acetamide, pyrimidine-2,4,5,6-tetramine and 2-(4,5-diamino-1H-pyrazol-1-yl)ethanol.

8. A system for coloring hair according to claim 6 wherein the system additionally comprises one or more couplers selected from the group consisting of: benzene-1,3-diol, 4-chlorobenzene-1,3-diol, naphthalen-1-ol, 2-methyl-naphthalen-1-ol, 2-methyl-benzene-1,3-diol, 2-(2,4-diamino-phenoxy)-ethanol, 2-(3-amino-4-methoxy-phenylamino)-ethanol, 2-[2,4-diamino-5-(2-hydroxy-ethoxy)-phenoxy]-ethanol, 3-(2,4-diamino-phenoxy)-propan-1-ol, 3-amino-phenol, 5-amino-2-methyl-phenol, 5-(2-hydroxy-ethylamino)-2-methyl-phenol, 3-amino-2-methyl-phenol, 3,4-dihydro-2H-1,4-benzoxazin-6-ol, 4-methyl-2-phenyl-2,4-dihydro-3H-pyrazol-3-one, and 1H-indol-6-ol, and 2-aminopyridin-3-ol.

9. A system for coloring hair according to claim 6 wherein the system additionally comprises one or more primary intermediates selected from the group consisting of: 2-methyl-benzene-1,4-diamine, benzene-1,4-diamine, 2-(2,5-diamino-phenyl)-ethanol, 1-(2,5-diamino-phenyl)-ethanol, 2-[(4-amino-phenyl)-(2-hydroxy-ethyl)-amino]-ethanol, 4-amino-phenol, 4-methylamino-phenol, 4-amino-3-methyl-phenol, 1-(5-amino-2-hydroxy-phenyl)-ethane-1,2-diol, 2-amino-phenol, 2-amino-5-methyl-phenol, 2-amino-6-methyl-phenol, N-(4-amino-3-hydroxy-phenyl)-acetamide, pyrimidine-2,4,5,6-tetramine and 2-(4,5-diamino-1H-pyrazol-1-yl)ethanol and one or more couplers selected from the group consisting of: benzene-1,3-diol, 4-chlorobenzene-1,3-diol, naphthalen-1-ol, 2-methyl-naphthalen-1-ol, 2-methyl-benzene-1,3-diol, 2-(2,4-diamino-phenoxy)-ethanol, 2-(3-amino-4-methoxy-phenylamino)-ethanol, 2-[2,4-diamino-5-(2-hydroxy-ethoxy)-phenoxy]-ethanol, 3-(2,4-diamino-phenoxy)-propan-1-ol, 3-amino-phenol, 5-amino-2-methyl-phenol, 5-(2-hydroxy-ethylamino)-2-methyl-phenol, 3-amino-2-methyl-phenol, 3,4-dihydro-2H-1,4-benzoxazin-6-ol, 4-methyl-2-phenyl-2,4-dihydro-3H-pyrazol-3-one, and 1H-indol-6-ol, and 2-aminopyridin-3-ol.

10. A system for coloring hair according to claim 6 wherein $R^1$ and $R^2$ are each $CH_3$; $R^4$ and $R^5$ are each hydrogen atoms; and X is selected from the group consisting of Cl, Br and $R^3SO_4$ where $R^3$ is $CH_3$ or $C_3H_7$.

11. A system for coloring hair according to claim 6 wherein R, $R^1$ and $R^2$ are each $CH_3$; $R^4$ and R5 are each hydrogen; and X is Cl or $R^3SO_4$ where $R^3$ is $CH_3$.

12. A hair coloring composition for dyeing human hair comprising, in a suitable carrier or vehicle, a dyeing effective amount of:

(a) at least one primary intermediate comprising a quaternized pyrrolidine compound of Formula (1):

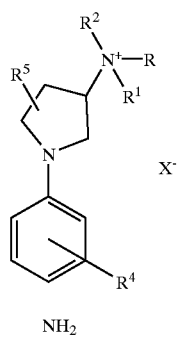

(1)

wherein X is selected from the group consisting of Cl, Br, I, or $R^3SO_4$; R is selected from the group consisting of a $C_1$ to $C_{22}$ alkyl group or a $C_1$ to $C_{22}$ mono or dihydroxyalkyl group; $R^1$ and $R^2$ are each independently a $C_1$ to C4 alkyl group; $R^3$ is a a $C_1$ to $C_{22}$ alkyl group or a $C_1$ to $C_{22}$ mono or dihydroxyalkyl group; $R^4$ is selected from the group consisting of a hydrogen atom, a $C_1$ to $C_5$ alkyl group or such an alkyl group substituted with one or more hydroxy or amino moieties; and $R^5$ is selected from the group consisting of a hydrogen atom or a hydroxy group (b) at least one coupler, and (c) at least one oxidizing agent.

13. A hair coloring composition according to claim 12 wherein $R^1$ and $R^2$ are each $CH_3$; $R^4$ and $R^5$ are each hydrogen atoms; and X is selected from the group consisting of Cl, Br and $R^3SO_4$ where $R^3$ is $CH_3$ or $C_3H_7$.

14. A hair coloring composition according to claim 12 wherein R, $R^1$ and $R^2$ are each $CH_3$; $R^4$ and $R^5$ are each hydrogen; and X is Cl or $R^3SO_4$ where $R^3$ is $CH_3$.

15. A process for dyeing human hair comprising applying a dyeing effective amount of a hair coloring composition of claim 12 to the hair and permitting the composition to contact the hair for a dyeing effective period of time, and then rinsing, shampooing and drying the hair.

16. A process for dyeing human hair comprising applying a dyeing effective amount of a hair coloring composition of claim 13 to the hair and permitting the composition to contact the hair for a dyeing effective period of time, and then rinsing, shampooing and drying the hair.

17. A process for dyeing human hair comprising applying a dyeing effective amount of a hair coloring composition of claim 14 to the hair and permitting the composition to contact the hair for a dyeing effective period of time, and then rinsing, shampooing and drying the hair.

18. A hair coloring system according to claim 4 wherein R is a $C_1$ to $C_6$ alkyl group.

19. A hair coloring system according to claim 10 wherein R is a $C_1$ to $C_6$ alkyl group.

20. A hair coloring system according to claim 13 wherein R is a $C_1$ to $C_6$ alkyl group.

* * * * *